United States Patent
Spivey et al.

(10) Patent No.: US 8,114,119 B2
(45) Date of Patent: Feb. 14, 2012

(54) SURGICAL GRASPING DEVICE

(75) Inventors: James T. Spivey, Cincinnati, OH (US); Rick D. Applegate, Florence, KY (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 533 days.

(21) Appl. No.: 12/207,306

(22) Filed: Sep. 9, 2008

(65) Prior Publication Data

US 2010/0063538 A1 Mar. 11, 2010

(51) Int. Cl.
*A16B 17/00* (2006.01)

(52) U.S. Cl. .................................. 606/205

(58) Field of Classification Search .......... 606/205–210, 606/139–147, 51–52, 120, 167, 170, 157–158, 606/79; 227/175.1; 600/104, 141–142, 214–216; 74/25; 192/43; 81/53.11, 53.12, 9.3, 316–318; 294/19.1
See application file for complete search history.

(56) References Cited

U.S. PATENT DOCUMENTS

| | | | |
|---|---|---|---|
| 645,576 A | 3/1900 | Tesla | |
| 649,621 A | 5/1900 | Tesla | |
| 787,412 A | 4/1905 | Tesla | |
| 1,127,948 A | 2/1915 | Wappler | |
| 1,482,653 A * | 2/1924 | Lilly | 81/53.11 |
| 1,625,602 A | 4/1927 | Gould et al. | |
| 2,028,635 A | 1/1936 | Wappler | |
| 2,113,246 A | 4/1938 | Wappler | |
| 2,155,365 A * | 4/1939 | Rankin | 294/19.1 |
| 2,191,858 A * | 2/1940 | Moore | 294/19.1 |
| 2,196,620 A | 4/1940 | Attarian | |
| 2,388,137 A * | 10/1945 | Graumlich | 81/53.11 |
| 2,493,108 A * | 1/1950 | Casey, Jr. | 294/19.1 |
| 2,504,152 A * | 4/1950 | Riker et al. | 81/53.11 |
| 2,938,382 A | 5/1960 | De Graaf | |
| 2,952,206 A | 9/1960 | Becksted | |
| 3,069,195 A * | 12/1962 | Buck | 81/53.12 |
| 3,170,471 A | 2/1965 | Schnitzer | |
| 3,435,824 A | 4/1969 | Gamponia | |
| 3,470,876 A | 10/1969 | Barchilon | |
| 3,669,487 A * | 6/1972 | Roberts et al. | 294/104 |

(Continued)

FOREIGN PATENT DOCUMENTS

AU 666310 B2 2/1996

(Continued)

OTHER PUBLICATIONS

Michael S. Kavic, M.D., "Natural Orifice Translumenal Endoscopic Surgery: "NOTES"", JSLS, vol. 10, pp. 133-134 (2006).

(Continued)

*Primary Examiner* — Gary Jackson
*Assistant Examiner* — Amy Shipley

(57) ABSTRACT

A surgical grasping device is disclosed. The surgical grasping device may comprise a clevis; a first jaw member pivotably coupled to the clevis; a second jaw member pivotably coupled to the clevis; and an actuating mechanism coupled to the clevis, the first jaw member and the second jaw member and a translating member coupled to and extending proximally from the actuating mechanism. The actuating mechanism may be configured to cause the first jaw member and the second jaw member to close in response to a first proximally directed force received via the translating member. The actuating mechanism may also be configured to cause the first jaw member and the second jaw member to open in response to a subsequent proximally directed force received via the translating member.

15 Claims, 19 Drawing Sheets

U.S. PATENT DOCUMENTS

| | | |
|---|---|---|
| 3,746,881 A | 7/1973 | Fitch et al. |
| 3,799,672 A | 3/1974 | Vurek |
| 3,854,473 A | 12/1974 | Matsuo |
| 3,946,740 A | 3/1976 | Bassett |
| 3,948,251 A | 4/1976 | Hosono |
| 3,994,301 A | 11/1976 | Agris |
| 4,011,872 A | 3/1977 | Komiya |
| 4,012,812 A | 3/1977 | Black |
| 4,164,225 A | 8/1979 | Johnson et al. |
| 4,178,920 A | 12/1979 | Cawood, Jr. et al. |
| 4,207,873 A | 6/1980 | Kruy |
| 4,235,238 A | 11/1980 | Ogiu et al. |
| 4,258,716 A | 3/1981 | Sutherland |
| 4,278,077 A | 7/1981 | Mizumoto |
| 4,285,344 A | 8/1981 | Marshall |
| 4,311,143 A | 1/1982 | Komiya |
| 4,329,980 A | 5/1982 | Terada |
| 4,396,021 A | 8/1983 | Baumgartner |
| 4,452,246 A | 6/1984 | Bader et al. |
| 4,461,281 A | 7/1984 | Carson |
| 4,491,132 A | 1/1985 | Aikins |
| 4,527,331 A | 7/1985 | Lasner et al. |
| 4,527,564 A | 7/1985 | Eguchi et al. |
| 4,538,594 A | 9/1985 | Boebel et al. |
| D281,104 S | 10/1985 | Davison |
| 4,569,347 A | 2/1986 | Frisbie |
| 4,580,551 A | 4/1986 | Siegmund et al. |
| 4,646,722 A | 3/1987 | Silverstein et al. |
| 4,653,476 A | 3/1987 | Bonnet |
| 4,669,470 A | 6/1987 | Brandfield |
| 4,671,477 A | 6/1987 | Cullen |
| 4,685,447 A | 8/1987 | Iversen et al. |
| 4,711,240 A | 12/1987 | Goldwasser et al. |
| 4,712,545 A | 12/1987 | Honkanen |
| 4,721,116 A | 1/1988 | Schintgen et al. |
| 4,733,662 A | 3/1988 | DeSatnick et al. |
| D295,894 S | 5/1988 | Sharkany et al. |
| 4,763,669 A | 8/1988 | Jaeger |
| 4,770,188 A | 9/1988 | Chikama |
| 4,815,450 A | 3/1989 | Patel |
| 4,823,794 A | 4/1989 | Pierce |
| 4,829,999 A | 5/1989 | Auth |
| 4,873,979 A | 10/1989 | Hanna |
| 4,880,015 A | 11/1989 | Nierman |
| 4,911,148 A | 3/1990 | Sosnowski et al. |
| 4,926,860 A | 5/1990 | Stice et al. |
| 4,938,214 A | 7/1990 | Specht et al. |
| 4,950,273 A | 8/1990 | Briggs |
| 4,950,285 A | 8/1990 | Wilk |
| 4,960,133 A | 10/1990 | Hewson |
| 4,977,887 A | 12/1990 | Gouda |
| 4,984,581 A | 1/1991 | Stice |
| 5,007,917 A | 4/1991 | Evans |
| 5,010,876 A | 4/1991 | Henley et al. |
| 5,020,514 A | 6/1991 | Heckele |
| 5,020,535 A | 6/1991 | Parker et al. |
| 5,025,778 A | 6/1991 | Silverstein et al. |
| 5,033,169 A | 7/1991 | Bindon |
| 5,037,433 A | 8/1991 | Wilk et al. |
| 5,041,129 A | 8/1991 | Hayhurst et al. |
| 5,046,513 A | 9/1991 | Gatturna et al. |
| 5,050,585 A | 9/1991 | Takahashi |
| 5,052,372 A | 10/1991 | Shapiro |
| 5,065,516 A | 11/1991 | Dulebohn |
| 5,066,295 A | 11/1991 | Kozak et al. |
| 5,123,913 A | 6/1992 | Wilk et al. |
| 5,123,914 A | 6/1992 | Cope |
| 5,133,727 A | 7/1992 | Bales et al. |
| 5,147,374 A | 9/1992 | Fernandez |
| 5,174,300 A | 12/1992 | Bales et al. |
| 5,176,126 A | 1/1993 | Chikama |
| 5,190,050 A | 3/1993 | Nitzsche |
| 5,190,555 A | 3/1993 | Wetter et al. |
| 5,192,284 A | 3/1993 | Pleatman |
| 5,201,752 A | 4/1993 | Brown et al. |
| 5,201,908 A | 4/1993 | Jones |
| 5,203,785 A | 4/1993 | Slater |
| 5,203,787 A | 4/1993 | Noblitt et al. |
| 5,209,747 A | 5/1993 | Knoepfler |
| 5,217,003 A | 6/1993 | Wilk |
| 5,217,453 A | 6/1993 | Wilk |
| 5,219,357 A | 6/1993 | Honkanen et al. |
| 5,219,358 A | 6/1993 | Bendel et al. |
| 5,222,362 A | 6/1993 | Maus et al. |
| 5,222,965 A | 6/1993 | Haughton |
| 5,234,437 A | 8/1993 | Sepetka |
| 5,234,453 A | 8/1993 | Smith et al. |
| 5,235,964 A | 8/1993 | Abenaim |
| 5,242,456 A | 9/1993 | Nash et al. |
| 5,246,424 A | 9/1993 | Wilk |
| 5,259,366 A | 11/1993 | Reydel et al. |
| 5,263,958 A | 11/1993 | deGuillebon et al. |
| 5,273,524 A | 12/1993 | Fox et al. |
| 5,275,607 A | 1/1994 | Lo et al. |
| 5,284,128 A | 2/1994 | Hart |
| 5,284,162 A | 2/1994 | Wilk |
| 5,287,845 A | 2/1994 | Faul et al. |
| 5,290,299 A | 3/1994 | Fain et al. |
| 5,290,302 A | 3/1994 | Pericic |
| 5,295,977 A | 3/1994 | Cohen et al. |
| 5,297,536 A | 3/1994 | Wilk |
| 5,301,061 A | 4/1994 | Nakada et al. |
| 5,312,333 A | 5/1994 | Churinetz et al. |
| 5,312,351 A | 5/1994 | Gerrone |
| 5,312,416 A | 5/1994 | Spaeth et al. |
| 5,312,423 A | 5/1994 | Rosenbluth et al. |
| 5,320,636 A | 6/1994 | Slater |
| 5,325,845 A | 7/1994 | Adair |
| 5,330,471 A | 7/1994 | Eggers |
| 5,330,486 A | 7/1994 | Wilk |
| 5,330,488 A | 7/1994 | Goldrath |
| 5,330,496 A | 7/1994 | Alferness |
| 5,330,502 A | 7/1994 | Hassler et al. |
| 5,331,971 A | 7/1994 | Bales et al. |
| 5,334,198 A | 8/1994 | Hart et al. |
| 5,344,428 A | 9/1994 | Griffiths |
| 5,350,391 A | 9/1994 | Iacovelli |
| 5,352,184 A | 10/1994 | Goldberg et al. |
| 5,352,222 A | 10/1994 | Rydell |
| 5,354,302 A | 10/1994 | Ko |
| 5,354,311 A | 10/1994 | Kambin et al. |
| 5,356,408 A | 10/1994 | Rydell |
| 5,364,408 A | 11/1994 | Gordon |
| 5,364,410 A | 11/1994 | Failla et al. |
| 5,366,466 A | 11/1994 | Christian et al. |
| 5,366,467 A | 11/1994 | Lynch et al. |
| 5,368,605 A | 11/1994 | Miller, Jr. |
| 5,370,647 A | 12/1994 | Graber et al. |
| 5,370,679 A | 12/1994 | Atlee, III |
| 5,374,273 A | 12/1994 | Nakao et al. |
| 5,374,275 A | 12/1994 | Bradley et al. |
| 5,374,277 A | 12/1994 | Hassler |
| 5,377,695 A | 1/1995 | An Haack |
| 5,383,877 A | 1/1995 | Clarke |
| 5,383,888 A | 1/1995 | Zvenyatsky et al. |
| 5,391,174 A | 2/1995 | Weston |
| 5,392,789 A | 2/1995 | Slater et al. |
| 5,395,386 A | 3/1995 | Slater |
| 5,401,248 A | 3/1995 | Bencini |
| 5,403,328 A | 4/1995 | Shallman |
| 5,403,342 A * | 4/1995 | Tovey et al. .................. 606/205 |
| 5,403,348 A | 4/1995 | Bonutti |
| 5,405,073 A | 4/1995 | Porter |
| 5,405,359 A | 4/1995 | Pierce |
| 5,409,478 A | 4/1995 | Gerry et al. |
| 5,417,699 A | 5/1995 | Klein et al. |
| 5,423,821 A | 6/1995 | Pasque |
| 5,433,721 A | 7/1995 | Hooven et al. |
| 5,439,471 A | 8/1995 | Kerr |
| 5,439,478 A | 8/1995 | Palmer |
| 5,441,059 A | 8/1995 | Dannan |
| 5,441,499 A | 8/1995 | Fritzsch |
| 5,449,021 A | 9/1995 | Chikama |
| 5,456,667 A | 10/1995 | Ham et al. |
| 5,456,684 A | 10/1995 | Schmidt et al. |
| 5,458,131 A | 10/1995 | Wilk |
| 5,458,583 A | 10/1995 | McNeely et al. |

| | | | | | |
|---|---|---|---|---|---|
| 5,460,168 A | 10/1995 | Masubuchi et al. | 5,746,759 A | 5/1998 | Meade et al. |
| 5,460,629 A | 10/1995 | Shlain et al. | 5,749,881 A | 5/1998 | Sackier et al. |
| 5,462,561 A | 10/1995 | Voda | 5,749,889 A | 5/1998 | Bacich et al. |
| 5,465,731 A | 11/1995 | Bell et al. | 5,752,951 A | 5/1998 | Yanik |
| 5,467,763 A | 11/1995 | McMahon et al. | 5,755,731 A | 5/1998 | Grinberg |
| 5,468,250 A | 11/1995 | Paraschac et al. | 5,766,167 A | 6/1998 | Eggers et al. |
| 5,470,308 A | 11/1995 | Edwards et al. | 5,766,170 A | 6/1998 | Eggers |
| 5,470,320 A | 11/1995 | Tiefenbrun et al. | 5,766,205 A | 6/1998 | Zvenyatsky et al. |
| 5,478,347 A | 12/1995 | Aranyi | 5,769,849 A | 6/1998 | Eggers |
| 5,480,404 A | 1/1996 | Kammerer et al. | 5,779,701 A | 7/1998 | McBrayer et al. |
| 5,482,054 A | 1/1996 | Slater et al. | 5,779,716 A | 7/1998 | Cano et al. |
| 5,484,451 A | 1/1996 | Akopov et al. | 5,779,727 A | 7/1998 | Orejola |
| 5,489,256 A | 2/1996 | Adair | 5,782,859 A | 7/1998 | Nicholas et al. |
| 5,496,347 A | 3/1996 | Hashiguchi et al. | 5,782,866 A | 7/1998 | Wenstrom, Jr. |
| 5,499,990 A | 3/1996 | Schülken et al. | 5,791,022 A | 8/1998 | Bohman |
| 5,499,992 A | 3/1996 | Meade et al. | 5,792,113 A | 8/1998 | Kramer et al. |
| 5,501,692 A | 3/1996 | Riza | 5,792,153 A | 8/1998 | Swain et al. |
| 5,503,616 A | 4/1996 | Jones | 5,792,165 A | 8/1998 | Klieman et al. |
| 5,505,686 A | 4/1996 | Willis et al. | 5,797,835 A | 8/1998 | Green |
| 5,507,755 A | 4/1996 | Gresl et al. | 5,797,928 A | 8/1998 | Kogasaka |
| 5,511,564 A | 4/1996 | Wilk | 5,797,939 A | 8/1998 | Yoon |
| 5,514,157 A | 5/1996 | Nicholas et al. | 5,797,941 A | 8/1998 | Schulze et al. |
| 5,522,829 A | 6/1996 | Michalos | 5,803,903 A | 9/1998 | Athas et al. |
| 5,522,830 A | 6/1996 | Aranyi | 5,808,665 A | 9/1998 | Green |
| 5,527,321 A | 6/1996 | Hinchliffe | 5,810,806 A | 9/1998 | Ritchart et al. |
| 5,540,648 A | 7/1996 | Yoon | 5,810,849 A | 9/1998 | Kontos |
| 5,554,151 A | 9/1996 | Hinchliffe | 5,810,865 A | 9/1998 | Koscher et al. |
| 5,555,883 A | 9/1996 | Avitall | 5,810,876 A | 9/1998 | Kelleher |
| 5,558,133 A | 9/1996 | Bortoli et al. | 5,810,877 A | 9/1998 | Roth et al. |
| 5,562,693 A | 10/1996 | Devlin et al. | 5,813,976 A | 9/1998 | Filipi et al. |
| 5,569,243 A | 10/1996 | Kortenbach et al. | 5,814,058 A | 9/1998 | Carlson et al. |
| 5,569,298 A | 10/1996 | Schnell | 5,817,061 A | 10/1998 | Goodwin et al. |
| 5,573,540 A | 11/1996 | Yoon | 5,817,107 A | 10/1998 | Schaller |
| 5,578,030 A | 11/1996 | Levin | 5,817,119 A | 10/1998 | Klieman et al. |
| 5,582,611 A | 12/1996 | Tsuruta et al. | 5,819,736 A | 10/1998 | Avny et al. |
| 5,582,617 A | 12/1996 | Klieman et al. | 5,827,281 A | 10/1998 | Levin |
| 5,584,845 A | 12/1996 | Hart | 5,827,299 A * | 10/1998 | Thomason et al. ............ 606/148 |
| 5,591,179 A | 1/1997 | Edelstein | 5,830,231 A | 11/1998 | Geiges, Jr. |
| 5,593,420 A | 1/1997 | Eubanks, Jr. et al. | 5,833,700 A | 11/1998 | Fogelberg et al. |
| 5,595,562 A | 1/1997 | Grier | 5,833,703 A | 11/1998 | Manushakian |
| 5,597,378 A | 1/1997 | Jervis | 5,843,017 A | 12/1998 | Yoon |
| 5,601,573 A | 2/1997 | Fogelberg et al. | 5,849,022 A | 12/1998 | Sakashita et al. |
| 5,601,588 A | 2/1997 | Tonomura et al. | 5,853,374 A | 12/1998 | Hart et al. |
| 5,604,531 A | 2/1997 | Iddan et al. | 5,855,585 A | 1/1999 | Kontos |
| 5,607,389 A | 3/1997 | Edwards et al. | 5,860,913 A | 1/1999 | Yamaya et al. |
| 5,607,450 A | 3/1997 | Zvenyatsky et al. | 5,860,995 A | 1/1999 | Berkelaar |
| 5,613,975 A | 3/1997 | Christy | 5,868,762 A | 2/1999 | Cragg et al. |
| 5,618,303 A | 4/1997 | Marlow et al. | 5,876,411 A | 3/1999 | Kontos |
| 5,620,415 A | 4/1997 | Lucey et al. | 5,882,331 A | 3/1999 | Sasaki |
| 5,624,399 A | 4/1997 | Ackerman | 5,882,344 A | 3/1999 | Stouder, Jr. |
| 5,624,431 A | 4/1997 | Gerry et al. | 5,893,846 A | 4/1999 | Bales et al. |
| 5,628,732 A | 5/1997 | Antoon, Jr. et al. | 5,893,874 A | 4/1999 | Bourque et al. |
| 5,630,782 A | 5/1997 | Adair | 5,893,875 A | 4/1999 | O'Connor et al. |
| 5,643,283 A | 7/1997 | Younker | 5,899,919 A | 5/1999 | Eubanks, Jr. et al. |
| 5,643,292 A | 7/1997 | Hart | 5,902,254 A | 5/1999 | Magram |
| 5,643,294 A | 7/1997 | Tovey et al. | 5,904,702 A | 5/1999 | Ek et al. |
| 5,644,798 A | 7/1997 | Shah | 5,908,420 A | 6/1999 | Parins et al. |
| 5,645,083 A | 7/1997 | Essig et al. | 5,916,147 A | 6/1999 | Boury |
| 5,649,372 A | 7/1997 | Souza | 5,921,993 A | 7/1999 | Yoon |
| 5,653,677 A | 8/1997 | Okada et al. | 5,921,997 A | 7/1999 | Fogelberg et al. |
| 5,653,722 A | 8/1997 | Kieturakis | 5,922,008 A | 7/1999 | Gimpelson |
| 5,662,663 A | 9/1997 | Shallman | 5,925,052 A | 7/1999 | Simmons |
| 5,669,875 A | 9/1997 | van Eerdenburg | 5,928,255 A | 7/1999 | Meade et al. |
| 5,681,324 A | 10/1997 | Kammerer et al. | 5,928,266 A | 7/1999 | Kontos |
| 5,681,330 A | 10/1997 | Hughett et al. | 5,936,536 A | 8/1999 | Morris |
| 5,685,820 A | 11/1997 | Riek et al. | 5,944,718 A | 8/1999 | Austin et al. |
| 5,690,656 A | 11/1997 | Cope et al. | 5,951,549 A | 9/1999 | Richardson et al. |
| 5,690,660 A | 11/1997 | Kauker et al. | 5,954,720 A | 9/1999 | Wilson et al. |
| 5,695,448 A | 12/1997 | Kimura et al. | 5,954,731 A | 9/1999 | Yoon |
| 5,695,505 A | 12/1997 | Yoon | 5,957,943 A | 9/1999 | Vaitekunas |
| 5,695,511 A | 12/1997 | Cano et al. | 5,957,953 A | 9/1999 | DiPoto et al. |
| 5,700,275 A * | 12/1997 | Bell et al. ...................... 606/208 | 5,971,995 A | 10/1999 | Rousseau |
| 5,702,438 A | 12/1997 | Avitall | 5,976,074 A | 11/1999 | Moriyama |
| 5,704,892 A | 1/1998 | Adair | 5,976,075 A | 11/1999 | Beane et al. |
| 5,709,708 A | 1/1998 | Thal | 5,976,130 A | 11/1999 | McBrayer et al. |
| 5,716,326 A | 2/1998 | Dannan | 5,976,131 A | 11/1999 | Guglielmi et al. |
| 5,730,740 A | 3/1998 | Wales et al. | 5,980,539 A | 11/1999 | Kontos |
| 5,741,278 A | 4/1998 | Stevens | 5,980,556 A | 11/1999 | Giordano et al. |
| 5,741,285 A | 4/1998 | McBrayer et al. | 5,984,938 A | 11/1999 | Yoon |

| | | | | | | |
|---|---|---|---|---|---|---|
| 5,989,182 | A | 11/1999 | Hori et al. | 6,447,511 B1 | 9/2002 | Slater |
| 5,993,447 | A | 11/1999 | Blewett et al. | 6,447,523 B1 | 9/2002 | Middleman et al. |
| 5,997,555 | A | 12/1999 | Kontos | 6,454,783 B1 | 9/2002 | Piskun |
| 6,001,120 | A | 12/1999 | Levin | 6,454,785 B2 | 9/2002 | De Hoyos Garza |
| 6,004,269 | A | 12/1999 | Crowley et al. | 6,464,701 B1 | 10/2002 | Hooven et al. |
| 6,004,330 | A | 12/1999 | Middleman et al. | 6,475,104 B1 | 11/2002 | Lutz et al. |
| 6,007,566 | A | 12/1999 | Wenstrom, Jr. | 6,485,411 B1 | 11/2002 | Konstorum et al. |
| 6,010,515 | A | 1/2000 | Swain et al. | 6,489,745 B1 | 12/2002 | Koreis |
| 6,012,494 | A | 1/2000 | Balazs | 6,491,626 B1 | 12/2002 | Stone et al. |
| 6,019,770 | A | 2/2000 | Christoudias | 6,491,691 B1 | 12/2002 | Morley et al. |
| 6,024,708 | A | 2/2000 | Bales et al. | 6,493,590 B1 | 12/2002 | Wessman et al. |
| 6,024,747 | A | 2/2000 | Kontos | 6,494,893 B2 | 12/2002 | Dubrul et al. |
| 6,027,522 | A | 2/2000 | Palmer | 6,503,192 B1 | 1/2003 | Ouchi |
| 6,030,365 | A | 2/2000 | Laufer | 6,506,190 B1 | 1/2003 | Walshe |
| 6,033,399 | A | 3/2000 | Gines | 6,508,827 B1 | 1/2003 | Manhes |
| 6,053,927 | A | 4/2000 | Hamas | 6,543,456 B1 | 4/2003 | Freeman |
| 6,066,160 | A | 5/2000 | Colvin et al. | 6,551,270 B1 | 4/2003 | Bimbo et al. |
| 6,068,603 | A | 5/2000 | Suzuki | 6,554,829 B2 | 4/2003 | Schulze et al. |
| 6,068,629 | A | 5/2000 | Haissaguerre et al. | 6,558,384 B2 | 5/2003 | Mayenberger |
| 6,071,233 | A | 6/2000 | Ishikawa et al. | 6,562,035 B1 | 5/2003 | Levin |
| 6,074,408 | A | 6/2000 | Freeman | 6,562,052 B2 | 5/2003 | Nobles et al. |
| 6,086,530 | A | 7/2000 | Mack | 6,569,159 B1 | 5/2003 | Edwards et al. |
| 6,090,108 | A | 7/2000 | McBrayer et al. | 6,572,629 B2 | 6/2003 | Kalloo et al. |
| 6,096,046 | A | 8/2000 | Weiss | 6,572,635 B1 | 6/2003 | Bonutti |
| 6,110,154 | A | 8/2000 | Shimomura et al. | 6,575,988 B2 | 6/2003 | Rousseau |
| 6,110,183 | A | 8/2000 | Cope | 6,579,311 B1 | 6/2003 | Makower |
| 6,113,593 | A | 9/2000 | Tu et al. | 6,585,642 B2 | 7/2003 | Christopher |
| 6,117,144 | A | 9/2000 | Nobles et al. | 6,585,717 B1 | 7/2003 | Wittenberger et al. |
| 6,117,158 | A * | 9/2000 | Measamer et al. ............ 606/208 | 6,592,559 B1 | 7/2003 | Pakter et al. |
| 6,139,555 | A | 10/2000 | Hart et al. | 6,592,603 B2 | 7/2003 | Lasner |
| 6,146,391 | A | 11/2000 | Cigaina | 6,602,262 B2 | 8/2003 | Griego et al. |
| 6,148,222 | A | 11/2000 | Ramsey, III | 6,605,105 B1 | 8/2003 | Cuschieri et al. |
| 6,149,653 | A | 11/2000 | Deslauriers | 6,610,072 B1 | 8/2003 | Christy et al. |
| 6,149,662 | A | 11/2000 | Pugliesi et al. | 6,610,074 B2 | 8/2003 | Santilli |
| 6,159,200 | A | 12/2000 | Verdura et al. | 6,620,193 B1 | 9/2003 | Lau et al. |
| 6,165,184 | A | 12/2000 | Verdura et al. | 6,626,919 B1 | 9/2003 | Swanstrom |
| 6,168,570 | B1 | 1/2001 | Ferrera | 6,632,229 B1 | 10/2003 | Yamanouchi |
| 6,168,605 | B1 | 1/2001 | Measamer et al. | 6,638,286 B1 | 10/2003 | Burbank et al. |
| 6,170,130 | B1 | 1/2001 | Hamilton et al. | 6,652,521 B1 | 11/2003 | Schulze |
| 6,179,776 | B1 | 1/2001 | Adams et al. | 6,652,551 B1 | 11/2003 | Heiss |
| 6,179,837 | B1 | 1/2001 | Hooven | 6,656,194 B1 | 12/2003 | Gannoe et al. |
| 6,183,420 | B1 | 2/2001 | Douk et al. | 6,663,641 B1 | 12/2003 | Kovac et al. |
| 6,190,353 | B1 | 2/2001 | Makower et al. | 6,666,854 B1 | 12/2003 | Lange |
| 6,190,384 | B1 | 2/2001 | Ouchi | 6,672,338 B1 | 1/2004 | Esashi et al. |
| 6,190,399 | B1 * | 2/2001 | Palmer et al. ................. 606/205 | 6,673,058 B2 | 1/2004 | Snow |
| 6,203,533 | B1 | 3/2001 | Ouchi | 6,673,087 B1 | 1/2004 | Chang et al. |
| 6,206,872 | B1 | 3/2001 | Lafond et al. | 6,685,628 B2 | 2/2004 | Vu |
| 6,206,877 | B1 | 3/2001 | Kese et al. | 6,685,724 B1 | 2/2004 | Haluck |
| 6,214,007 | B1 | 4/2001 | Anderson | 6,692,445 B2 | 2/2004 | Roberts et al. |
| 6,228,096 | B1 | 5/2001 | Marchand | 6,692,462 B2 | 2/2004 | Mackenzie et al. |
| 6,245,079 | B1 | 6/2001 | Nobles et al. | 6,699,180 B2 | 3/2004 | Kobayashi |
| 6,246,914 | B1 | 6/2001 | de la Rama et al. | 6,699,256 B1 | 3/2004 | Logan et al. |
| 6,258,064 | B1 | 7/2001 | Smith et al. | 6,699,263 B2 | 3/2004 | Cope |
| 6,261,242 | B1 | 7/2001 | Roberts et al. | 6,706,018 B2 | 3/2004 | Westlund et al. |
| 6,264,664 | B1 | 7/2001 | Avellanet | 6,708,066 B2 | 3/2004 | Herbst et al. |
| 6,270,497 | B1 | 8/2001 | Sekino et al. | 6,716,226 B2 | 4/2004 | Sixto, Jr. et al. |
| 6,270,505 | B1 | 8/2001 | Yoshida et al. | 6,736,822 B2 | 5/2004 | McClellan et al. |
| 6,277,136 | B1 | 8/2001 | Bonutti | 6,740,030 B2 | 5/2004 | Martone et al. |
| 6,283,963 | B1 | 9/2001 | Regula | 6,743,240 B2 | 6/2004 | Smith et al. |
| 6,293,909 | B1 | 9/2001 | Chu et al. | 6,749,560 B1 | 6/2004 | Konstorum et al. |
| 6,293,952 | B1 | 9/2001 | Brosens et al. | 6,749,609 B1 | 6/2004 | Lunsford et al. |
| 6,296,630 | B1 | 10/2001 | Altman et al. | 6,752,768 B2 | 6/2004 | Burdorff et al. |
| 6,322,578 | B1 | 11/2001 | Houle et al. | 6,752,811 B2 | 6/2004 | Chu et al. |
| 6,326,177 | B1 | 12/2001 | Schoenbach et al. | 6,752,822 B2 | 6/2004 | Jespersen |
| 6,328,730 | B1 | 12/2001 | Harkrider, Jr. | 6,761,685 B2 | 7/2004 | Adams et al. |
| 6,350,267 | B1 | 2/2002 | Stefanchik | 6,761,718 B2 | 7/2004 | Madsen |
| 6,350,278 | B1 | 2/2002 | Lenker et al. | 6,773,434 B2 | 8/2004 | Ciarrocca |
| 6,352,503 | B1 | 3/2002 | Matsui et al. | 6,780,151 B2 | 8/2004 | Grabover et al. |
| 6,352,543 | B1 | 3/2002 | Cole | 6,780,352 B2 | 8/2004 | Jacobson |
| 6,355,035 | B1 | 3/2002 | Manushakian | 6,783,491 B2 | 8/2004 | Saadat et al. |
| 6,371,956 | B1 | 4/2002 | Wilson et al. | 6,786,864 B2 | 9/2004 | Matsuura et al. |
| 6,379,366 | B1 | 4/2002 | Fleischman et al. | 6,790,173 B2 | 9/2004 | Saadat et al. |
| 6,383,195 | B1 | 5/2002 | Richard | 6,795,728 B2 | 9/2004 | Chornenky et al. |
| 6,383,197 | B1 | 5/2002 | Conlon et al. | 6,800,056 B2 | 10/2004 | Tartaglia et al. |
| 6,391,029 | B1 | 5/2002 | Hooven et al. | 6,808,491 B2 | 10/2004 | Kortenbach et al. |
| 6,402,735 | B1 | 6/2002 | Langevin | 6,824,548 B2 | 11/2004 | Smith et al. |
| 6,406,440 | B1 | 6/2002 | Stefanchik | 6,837,847 B2 | 1/2005 | Ewers et al. |
| 6,409,733 | B1 | 6/2002 | Conlon et al. | 6,843,794 B2 | 1/2005 | Sixto, Jr. et al. |
| 6,431,500 | B1 | 8/2002 | Jacobs et al. | 6,861,250 B1 | 3/2005 | Cole et al. |

| | | |
|---|---|---|
| 6,866,627 B2 | 3/2005 | Nozue |
| 6,878,106 B1 | 4/2005 | Herrmann |
| 6,878,110 B2 | 4/2005 | Yang et al. |
| 6,884,213 B2 | 4/2005 | Raz et al. |
| 6,887,255 B2 | 5/2005 | Shimm |
| 6,896,683 B1 | 5/2005 | Gadberry et al. |
| 6,908,427 B2 | 6/2005 | Fleener et al. |
| 6,908,476 B2 | 6/2005 | Jud et al. |
| 6,916,284 B2 | 7/2005 | Moriyama |
| 6,918,871 B2 | 7/2005 | Schulze |
| 6,926,725 B2 | 8/2005 | Cooke et al. |
| 6,932,810 B2 | 8/2005 | Ryan |
| 6,932,824 B1 | 8/2005 | Roop et al. |
| 6,932,827 B2 | 8/2005 | Cole |
| 6,939,327 B2 | 9/2005 | Hall et al. |
| 6,942,613 B2 | 9/2005 | Ewers et al. |
| 6,945,472 B2 * | 9/2005 | Wuttke et al. ............... 239/321 |
| 6,945,979 B2 | 9/2005 | Kortenbach et al. |
| 6,958,035 B2 | 10/2005 | Friedman et al. |
| 6,960,162 B2 | 11/2005 | Saadat et al. |
| 6,960,163 B2 | 11/2005 | Ewers et al. |
| 6,962,587 B2 | 11/2005 | Johnson et al. |
| 6,964,662 B2 | 11/2005 | Kidooka |
| 6,966,909 B2 | 11/2005 | Marshall et al. |
| 6,966,919 B2 | 11/2005 | Sixto, Jr. et al. |
| 6,967,462 B1 | 11/2005 | Landis |
| 6,971,988 B2 | 12/2005 | Orban, III |
| 6,972,017 B2 | 12/2005 | Smith et al. |
| 6,974,411 B2 | 12/2005 | Belson |
| 6,976,992 B2 | 12/2005 | Sachatello et al. |
| 6,984,203 B2 | 1/2006 | Tartaglia et al. |
| 6,984,205 B2 | 1/2006 | Gazdzinski |
| 6,986,774 B2 | 1/2006 | Middleman et al. |
| 6,988,987 B2 | 1/2006 | Ishikawa et al. |
| 6,989,028 B2 | 1/2006 | Lashinski et al. |
| 6,991,627 B2 | 1/2006 | Madhani et al. |
| 6,994,708 B2 | 2/2006 | Manzo |
| 6,997,931 B2 | 2/2006 | Sauer et al. |
| 7,000,818 B2 | 2/2006 | Shelton, IV et al. |
| 7,008,375 B2 | 3/2006 | Weisel |
| 7,009,634 B2 | 3/2006 | Iddan et al. |
| 7,010,340 B2 | 3/2006 | Scarantino et al. |
| 7,020,531 B1 | 3/2006 | Colliou et al. |
| 7,025,580 B2 | 4/2006 | Heagy et al. |
| 7,029,435 B2 | 4/2006 | Nakao |
| 7,029,438 B2 | 4/2006 | Morin et al. |
| 7,035,680 B2 | 4/2006 | Partridge et al. |
| 7,037,290 B2 | 5/2006 | Gardeski et al. |
| 7,041,052 B2 | 5/2006 | Saadat et al. |
| 7,052,489 B2 | 5/2006 | Griego et al. |
| 7,060,024 B2 | 6/2006 | Long et al. |
| 7,060,025 B2 | 6/2006 | Long et al. |
| 7,063,697 B2 | 6/2006 | Slater |
| 7,063,715 B2 | 6/2006 | Onuki et al. |
| 7,066,879 B2 | 6/2006 | Fowler et al. |
| 7,066,936 B2 | 6/2006 | Ryan |
| 7,070,602 B2 | 7/2006 | Smith et al. |
| 7,076,305 B2 | 7/2006 | Imran et al. |
| 7,083,629 B2 | 8/2006 | Weller et al. |
| 7,087,071 B2 | 8/2006 | Nicholas et al. |
| 7,090,673 B2 | 8/2006 | Dycus et al. |
| 7,090,685 B2 | 8/2006 | Kortenbach et al. |
| 7,093,518 B2 * | 8/2006 | Gmeilbauer ............... 81/9.3 |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,105,000 B2 | 9/2006 | McBrayer |
| 7,105,005 B2 | 9/2006 | Blake |
| 7,108,703 B2 | 9/2006 | Danitz et al. |
| 7,112,208 B2 | 9/2006 | Morris et al. |
| 7,115,092 B2 | 10/2006 | Park et al. |
| 7,118,531 B2 | 10/2006 | Krill |
| 7,118,578 B2 | 10/2006 | West, Jr. et al. |
| 7,118,587 B2 | 10/2006 | Dycus et al. |
| 7,128,708 B2 | 10/2006 | Saadat et al. |
| RE39,415 E | 11/2006 | Bales et al. |
| 7,131,978 B2 | 11/2006 | Sancoff et al. |
| 7,131,979 B2 | 11/2006 | DiCarlo et al. |
| 7,131,980 B1 | 11/2006 | Field et al. |
| 7,137,980 B2 | 11/2006 | Buysse et al. |
| 7,137,981 B2 | 11/2006 | Long |
| 7,146,984 B2 | 12/2006 | Stack et al. |
| 7,147,650 B2 | 12/2006 | Lee |
| 7,153,321 B2 | 12/2006 | Andrews |
| 7,163,525 B2 | 1/2007 | Franer |
| 7,172,714 B2 | 2/2007 | Jacobson |
| 7,179,254 B2 | 2/2007 | Pendekanti et al. |
| 7,195,612 B2 | 3/2007 | Van Sloten et al. |
| 7,195,631 B2 | 3/2007 | Dumbauld |
| 7,208,005 B2 | 4/2007 | Frecker et al. |
| 7,211,092 B2 | 5/2007 | Hughett |
| 7,223,272 B2 | 5/2007 | Francese et al. |
| 7,232,414 B2 | 6/2007 | Gonzalez |
| 7,232,445 B2 | 6/2007 | Kortenbach et al. |
| 7,241,290 B2 | 7/2007 | Doyle et al. |
| 7,244,228 B2 | 7/2007 | Lubowski |
| 7,252,660 B2 | 8/2007 | Kunz |
| 7,270,663 B2 | 9/2007 | Nakao |
| 7,294,139 B1 | 11/2007 | Gengler |
| 7,301,250 B2 | 11/2007 | Cassel |
| 7,306,597 B2 | 12/2007 | Manzo |
| 7,318,802 B2 | 1/2008 | Suzuki et al. |
| 7,320,695 B2 | 1/2008 | Carroll |
| 7,322,934 B2 | 1/2008 | Miyake et al. |
| 7,323,006 B2 | 1/2008 | Andreas et al. |
| 7,329,257 B2 | 2/2008 | Kanehira et al. |
| 7,329,383 B2 | 2/2008 | Stinson |
| 7,344,536 B1 | 3/2008 | Lunsford et al. |
| 7,352,387 B2 | 4/2008 | Yamamoto |
| 7,364,582 B2 | 4/2008 | Lee |
| 7,371,215 B2 | 5/2008 | Colliou et al. |
| 7,381,216 B2 | 6/2008 | Buzzard et al. |
| 7,393,322 B2 | 7/2008 | Wenchell |
| 7,402,162 B2 | 7/2008 | Ouchi |
| 7,404,791 B2 | 7/2008 | Linares et al. |
| 7,413,563 B2 | 8/2008 | Corcoran et al. |
| 7,416,554 B2 | 8/2008 | Lam et al. |
| 7,422,590 B2 | 9/2008 | Kupferschmid et al. |
| 7,435,257 B2 | 10/2008 | Lashinski et al. |
| 7,452,327 B2 | 11/2008 | Durgin et al. |
| 7,468,066 B2 | 12/2008 | Vargas et al. |
| 7,488,295 B2 | 2/2009 | Burbank et al. |
| 7,497,867 B2 | 3/2009 | Lasner et al. |
| 7,507,200 B2 | 3/2009 | Okada |
| 7,524,281 B2 | 4/2009 | Chu et al. |
| 7,524,302 B2 | 4/2009 | Tower |
| 7,534,228 B2 | 5/2009 | Williams |
| 7,544,203 B2 | 6/2009 | Chin et al. |
| 7,548,040 B2 | 6/2009 | Lee et al. |
| 7,549,564 B2 | 6/2009 | Boudreaux |
| 7,553,278 B2 | 6/2009 | Kucklick |
| 7,553,298 B2 | 6/2009 | Hunt et al. |
| 7,559,887 B2 | 7/2009 | Dannan |
| 7,560,006 B2 | 7/2009 | Rakos et al. |
| 7,561,916 B2 | 7/2009 | Hunt et al. |
| 7,566,334 B2 * | 7/2009 | Christian et al. ............... 606/51 |
| 7,575,144 B2 | 8/2009 | Ortiz et al. |
| 7,579,550 B2 | 8/2009 | Dayton et al. |
| 7,582,096 B2 | 9/2009 | Gellman et al. |
| 7,588,177 B2 | 9/2009 | Racenet |
| 7,588,557 B2 | 9/2009 | Nakao |
| 7,618,398 B2 | 11/2009 | Holman et al. |
| 7,632,250 B2 | 12/2009 | Smith et al. |
| 7,635,373 B2 | 12/2009 | Ortiz |
| 7,637,903 B2 | 12/2009 | Lentz et al. |
| 7,651,483 B2 | 1/2010 | Byrum et al. |
| 7,651,509 B2 | 1/2010 | Bojarski et al. |
| 7,654,431 B2 * | 2/2010 | Hueil et al. ............... 227/175.1 |
| 7,662,089 B2 | 2/2010 | Okada et al. |
| 7,666,180 B2 | 2/2010 | Holsten et al. |
| 7,713,270 B2 | 5/2010 | Suzuki |
| 7,736,374 B2 | 6/2010 | Vaughan et al. |
| 7,762,998 B2 | 7/2010 | Birk et al. |
| 7,771,416 B2 | 8/2010 | Spivey et al. |
| 7,780,683 B2 | 8/2010 | Roue et al. |
| 7,794,475 B2 | 9/2010 | Hess et al. |
| 7,837,615 B2 | 11/2010 | Le et al. |
| 7,850,660 B2 | 12/2010 | Uth et al. |

| | | |
|---|---|---|
| 7,857,183 B2 | 12/2010 | Shelton, IV |
| 7,862,546 B2 | 1/2011 | Conlon et al. |
| 7,867,216 B2 | 1/2011 | Wahr et al. |
| 7,896,887 B2 | 3/2011 | Rimbaugh et al. |
| 7,918,869 B2 | 4/2011 | Saadat et al. |
| 7,931,624 B2 | 4/2011 | Smith et al. |
| 7,947,000 B2 | 5/2011 | Vargas et al. |
| 7,955,298 B2 | 6/2011 | Carroll et al. |
| 7,963,975 B2 | 6/2011 | Criscuolo |
| 2001/0049497 A1 | 12/2001 | Kalloo et al. |
| 2002/0022771 A1 | 2/2002 | Diokno et al. |
| 2002/0022857 A1 | 2/2002 | Goldsteen et al. |
| 2002/0023353 A1 | 2/2002 | Ting-Kung |
| 2002/0042562 A1 | 4/2002 | Meron et al. |
| 2002/0049439 A1 | 4/2002 | Mulier et al. |
| 2002/0068945 A1 | 6/2002 | Sixto, Jr. et al. |
| 2002/0078967 A1 | 6/2002 | Sixto, Jr. et al. |
| 2002/0082516 A1 | 6/2002 | Stefanchik |
| 2002/0091391 A1 | 7/2002 | Cole et al. |
| 2002/0095164 A1 | 7/2002 | Andreas et al. |
| 2002/0107530 A1 | 8/2002 | Sauer et al. |
| 2002/0133115 A1 | 9/2002 | Gordon et al. |
| 2002/0138086 A1 | 9/2002 | Sixto, Jr. et al. |
| 2002/0147456 A1 | 10/2002 | Diduch et al. |
| 2002/0183591 A1 | 12/2002 | Matsuura et al. |
| 2003/0023255 A1 | 1/2003 | Miles et al. |
| 2003/0036679 A1 | 2/2003 | Kortenbach et al. |
| 2003/0069602 A1 | 4/2003 | Jacobs et al. |
| 2003/0083681 A1 | 5/2003 | Moutafis et al. |
| 2003/0114732 A1 | 6/2003 | Webler et al. |
| 2003/0120257 A1 | 6/2003 | Houston et al. |
| 2003/0130564 A1 | 7/2003 | Martone et al. |
| 2003/0130656 A1 | 7/2003 | Levin |
| 2003/0158521 A1 | 8/2003 | Ameri |
| 2003/0167062 A1 | 9/2003 | Gambale et al. |
| 2003/0171651 A1 | 9/2003 | Page et al. |
| 2003/0176880 A1 | 9/2003 | Long et al. |
| 2003/0191497 A1 | 10/2003 | Cope |
| 2003/0195565 A1 | 10/2003 | Bonutti |
| 2003/0216611 A1 | 11/2003 | Vu |
| 2003/0216615 A1 | 11/2003 | Ouchi |
| 2003/0220545 A1 | 11/2003 | Ouchi |
| 2003/0225312 A1 | 12/2003 | Suzuki et al. |
| 2003/0225332 A1 | 12/2003 | Okada et al. |
| 2003/0229269 A1 | 12/2003 | Humphrey |
| 2003/0229371 A1 | 12/2003 | Whitworth |
| 2003/0236549 A1 | 12/2003 | Bonadio et al. |
| 2004/0002683 A1 | 1/2004 | Nicholson et al. |
| 2004/0002735 A1 | 1/2004 | Lizardi et al. |
| 2004/0034369 A1 | 2/2004 | Sauer et al. |
| 2004/0098007 A1 | 5/2004 | Heiss |
| 2004/0101456 A1 | 5/2004 | Kuroshima et al. |
| 2004/0116948 A1 | 6/2004 | Sixto, Jr. et al. |
| 2004/0133077 A1 | 7/2004 | Obenchain et al. |
| 2004/0133089 A1 | 7/2004 | Kilcoyne et al. |
| 2004/0136779 A1 | 7/2004 | Bhaskar |
| 2004/0138525 A1 | 7/2004 | Saadat et al. |
| 2004/0138529 A1 | 7/2004 | Wiltshire et al. |
| 2004/0138587 A1 | 7/2004 | Lyons, IV |
| 2004/0186350 A1 | 9/2004 | Brenneman et al. |
| 2004/0193009 A1 | 9/2004 | Jaffe et al. |
| 2004/0193146 A1 | 9/2004 | Lee et al. |
| 2004/0193186 A1 | 9/2004 | Kortenbach et al. |
| 2004/0193188 A1 | 9/2004 | Francese |
| 2004/0193189 A1 | 9/2004 | Kortenbach et al. |
| 2004/0193200 A1 | 9/2004 | Dworschak et al. |
| 2004/0199052 A1 | 10/2004 | Banik et al. |
| 2004/0210245 A1 | 10/2004 | Erickson et al. |
| 2004/0215058 A1 | 10/2004 | Zirps et al. |
| 2004/0225183 A1 | 11/2004 | Michlitsch et al. |
| 2004/0225186 A1 | 11/2004 | Horne, Jr. et al. |
| 2004/0230095 A1 | 11/2004 | Stefanchik et al. |
| 2004/0230096 A1 | 11/2004 | Stefanchik et al. |
| 2004/0230097 A1 | 11/2004 | Stefanchik et al. |
| 2004/0230161 A1 | 11/2004 | Zeiner |
| 2004/0249246 A1 | 12/2004 | Campos |
| 2004/0249367 A1 | 12/2004 | Saadat et al. |
| 2004/0249394 A1 | 12/2004 | Morris et al. |
| 2004/0249443 A1 | 12/2004 | Shanley et al. |
| 2005/0004515 A1 | 1/2005 | Hart et al. |
| 2005/0033265 A1 | 2/2005 | Engel et al. |
| 2005/0033277 A1 | 2/2005 | Clague et al. |
| 2005/0033319 A1 | 2/2005 | Gambale et al. |
| 2005/0033333 A1 | 2/2005 | Smith et al. |
| 2005/0043690 A1 | 2/2005 | Todd |
| 2005/0049616 A1 | 3/2005 | Rivera et al. |
| 2005/0065397 A1 | 3/2005 | Saadat et al. |
| 2005/0065517 A1 | 3/2005 | Chin |
| 2005/0070754 A1 | 3/2005 | Nobis et al. |
| 2005/0070763 A1 | 3/2005 | Nobis et al. |
| 2005/0070764 A1 | 3/2005 | Nobis et al. |
| 2005/0080413 A1 | 4/2005 | Canady |
| 2005/0085693 A1 | 4/2005 | Belson et al. |
| 2005/0085832 A1 | 4/2005 | Sancoff et al. |
| 2005/0090837 A1 | 4/2005 | Sixto, Jr. et al. |
| 2005/0090838 A1 | 4/2005 | Sixto, Jr. et al. |
| 2005/0101837 A1 | 5/2005 | Kalloo et al. |
| 2005/0101838 A1 | 5/2005 | Camillocci et al. |
| 2005/0107663 A1 | 5/2005 | Saadat et al. |
| 2005/0107664 A1 | 5/2005 | Kalloo et al. |
| 2005/0110881 A1 | 5/2005 | Glukhovsky et al. |
| 2005/0113847 A1 | 5/2005 | Gadberry et al. |
| 2005/0124855 A1 | 6/2005 | Jaffe et al. |
| 2005/0125010 A1 | 6/2005 | Smith et al. |
| 2005/0131279 A1 | 6/2005 | Boulais et al. |
| 2005/0131457 A1 | 6/2005 | Douglas et al. |
| 2005/0137454 A1 | 6/2005 | Saadat et al. |
| 2005/0143647 A1 | 6/2005 | Minai et al. |
| 2005/0143690 A1 | 6/2005 | High |
| 2005/0143774 A1 | 6/2005 | Polo |
| 2005/0143803 A1 | 6/2005 | Watson et al. |
| 2005/0149087 A1 | 7/2005 | Ahlberg et al. |
| 2005/0149096 A1 | 7/2005 | Hilal et al. |
| 2005/0159648 A1 | 7/2005 | Freed |
| 2005/0165272 A1 | 7/2005 | Okada et al. |
| 2005/0165378 A1 | 7/2005 | Heinrich et al. |
| 2005/0165411 A1 | 7/2005 | Orban, III |
| 2005/0165429 A1 | 7/2005 | Douglas et al. |
| 2005/0182429 A1 | 8/2005 | Yamanouchi |
| 2005/0192478 A1 | 9/2005 | Williams et al. |
| 2005/0192598 A1 | 9/2005 | Johnson et al. |
| 2005/0192602 A1 | 9/2005 | Manzo |
| 2005/0192654 A1 | 9/2005 | Chanduszko et al. |
| 2005/0209624 A1 | 9/2005 | Vijay |
| 2005/0215858 A1 | 9/2005 | Vail, III |
| 2005/0216050 A1 | 9/2005 | Sepetka et al. |
| 2005/0228406 A1 | 10/2005 | Bose |
| 2005/0234297 A1 | 10/2005 | Devierre et al. |
| 2005/0250983 A1 | 11/2005 | Tremaglio et al. |
| 2005/0250990 A1 | 11/2005 | Le et al. |
| 2005/0250993 A1 | 11/2005 | Jaeger |
| 2005/0251166 A1 | 11/2005 | Vaughan et al. |
| 2005/0251176 A1 | 11/2005 | Swanstrom et al. |
| 2005/0261674 A1 | 11/2005 | Nobis et al. |
| 2005/0267492 A1 | 12/2005 | Poncet et al. |
| 2005/0272975 A1 | 12/2005 | McWeeney et al. |
| 2005/0272977 A1 | 12/2005 | Saadat et al. |
| 2005/0273084 A1 | 12/2005 | Hinman et al. |
| 2005/0277945 A1 | 12/2005 | Saadat et al. |
| 2005/0277951 A1 | 12/2005 | Smith et al. |
| 2005/0277952 A1 | 12/2005 | Arp et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277957 A1 | 12/2005 | Kuhns et al. |
| 2005/0283118 A1 | 12/2005 | Uth et al. |
| 2005/0283119 A1 | 12/2005 | Uth et al. |
| 2005/0288555 A1 | 12/2005 | Binmoeller |
| 2006/0004406 A1 | 1/2006 | Wehrstein et al. |
| 2006/0004409 A1 | 1/2006 | Nobis et al. |
| 2006/0004410 A1 | 1/2006 | Nobis et al. |
| 2006/0015009 A1 | 1/2006 | Jaffe et al. |
| 2006/0020167 A1 | 1/2006 | Sitzmann |
| 2006/0020247 A1 | 1/2006 | Kagan et al. |
| 2006/0025654 A1 | 2/2006 | Suzuki et al. |
| 2006/0025781 A1 | 2/2006 | Young et al. |
| 2006/0025812 A1 | 2/2006 | Shelton, IV |
| 2006/0025819 A1 | 2/2006 | Nobis et al. |

| | | | | | | |
|---|---|---|---|---|---|---|
| 2006/0036267 A1 | 2/2006 | Saadat et al. | | 2007/0049800 A1 | 3/2007 | Boulais |
| 2006/0041188 A1 | 2/2006 | Dirusso et al. | | 2007/0049902 A1 | 3/2007 | Griffin et al. |
| 2006/0058582 A1 | 3/2006 | Maahs et al. | | 2007/0051375 A1 | 3/2007 | Milliman |
| 2006/0058776 A1 | 3/2006 | Bilsbury | | 2007/0060880 A1 | 3/2007 | Gregorich et al. |
| 2006/0069396 A1 | 3/2006 | Meade et al. | | 2007/0067017 A1 | 3/2007 | Trapp |
| 2006/0069424 A1 | 3/2006 | Acosta et al. | | 2007/0073102 A1 | 3/2007 | Matsuno et al. |
| 2006/0074413 A1 | 4/2006 | Behzadian | | 2007/0073269 A1 | 3/2007 | Becker |
| 2006/0079890 A1 | 4/2006 | Guerra | | 2007/0079924 A1 | 4/2007 | Saadat et al. |
| 2006/0089528 A1 | 4/2006 | Tartaglia et al. | | 2007/0088370 A1 | 4/2007 | Kahle et al. |
| 2006/0095060 A1 | 5/2006 | Mayenberger et al. | | 2007/0100375 A1 | 5/2007 | Mikkaichi et al. |
| 2006/0100687 A1 | 5/2006 | Fahey et al. | | 2007/0100376 A1 | 5/2007 | Mikkaichi et al. |
| 2006/0106423 A1 | 5/2006 | Weisel et al. | | 2007/0106118 A1 | 5/2007 | Moriyama |
| 2006/0111209 A1 | 5/2006 | Hinman et al. | | 2007/0112251 A1 | 5/2007 | Nakhuda |
| 2006/0111210 A1 | 5/2006 | Hinman et al. | | 2007/0112331 A1 | 5/2007 | Weber et al. |
| 2006/0111704 A1 | 5/2006 | Brenneman et al. | | 2007/0112342 A1 | 5/2007 | Pearson et al. |
| 2006/0129166 A1 | 6/2006 | Lavelle | | 2007/0112383 A1 | 5/2007 | Conlon et al. |
| 2006/0135962 A1 | 6/2006 | Kick et al. | | 2007/0112384 A1 | 5/2007 | Conlon et al. |
| 2006/0135971 A1 | 6/2006 | Swanstrom et al. | | 2007/0112385 A1 | 5/2007 | Conlon |
| 2006/0135984 A1 | 6/2006 | Kramer et al. | | 2007/0112417 A1 | 5/2007 | Shanley et al. |
| 2006/0142644 A1 | 6/2006 | Mulac et al. | | 2007/0112425 A1 | 5/2007 | Schaller et al. |
| 2006/0142652 A1 | 6/2006 | Keenan | | 2007/0118115 A1 | 5/2007 | Artale et al. |
| 2006/0142790 A1 | 6/2006 | Gertner | | 2007/0123840 A1 | 5/2007 | Cox |
| 2006/0142798 A1 | 6/2006 | Holman et al. | | 2007/0129605 A1 | 6/2007 | Schaaf |
| 2006/0149132 A1 | 7/2006 | Iddan | | 2007/0129719 A1 | 6/2007 | Kendale et al. |
| 2006/0149135 A1 | 7/2006 | Paz | | 2007/0129760 A1 | 6/2007 | Demarais et al. |
| 2006/0161190 A1 | 7/2006 | Gadberry et al. | | 2007/0135709 A1 | 6/2007 | Rioux et al. |
| 2006/0167416 A1 | 7/2006 | Mathis et al. | | 2007/0142706 A1 | 6/2007 | Matsui et al. |
| 2006/0167482 A1 | 7/2006 | Swain et al. | | 2007/0156127 A1 | 7/2007 | Rioux et al. |
| 2006/0178560 A1 | 8/2006 | Saadat et al. | | 2007/0161855 A1 | 7/2007 | Mikkaichi et al. |
| 2006/0183975 A1 | 8/2006 | Saadat et al. | | 2007/0173691 A1 | 7/2007 | Yokoi et al. |
| 2006/0184161 A1 | 8/2006 | Maahs et al. | | 2007/0173869 A1 | 7/2007 | Gannoe et al. |
| 2006/0189844 A1 | 8/2006 | Tien | | 2007/0173870 A2 | 7/2007 | Zacharias |
| 2006/0189845 A1 | 8/2006 | Maahs et al. | | 2007/0173872 A1 | 7/2007 | Neuenfeldt |
| 2006/0190027 A1 | 8/2006 | Downey | | 2007/0179525 A1 | 8/2007 | Frecker et al. |
| 2006/0190031 A1* | 8/2006 | Wales et al. .................. 606/205 | | 2007/0179530 A1 | 8/2007 | Tieu et al. |
| 2006/0195084 A1 | 8/2006 | Slater | | 2007/0197865 A1 | 8/2007 | Miyake et al. |
| 2006/0200005 A1 | 9/2006 | Bjork et al. | | 2007/0198057 A1 | 8/2007 | Gelbart et al. |
| 2006/0200169 A1 | 9/2006 | Sniffin | | 2007/0203487 A1 | 8/2007 | Sugita |
| 2006/0200170 A1 | 9/2006 | Aranyi | | 2007/0208364 A1 | 9/2007 | Smith et al. |
| 2006/0200199 A1 | 9/2006 | Bonutti et al. | | 2007/0213754 A1 | 9/2007 | Mikkaichi et al. |
| 2006/0217665 A1 | 9/2006 | Prosek | | 2007/0225554 A1 | 9/2007 | Maseda et al. |
| 2006/0217697 A1 | 9/2006 | Lau et al. | | 2007/0233040 A1 | 10/2007 | Macnamara et al. |
| 2006/0217742 A1 | 9/2006 | Messerly et al. | | 2007/0244358 A1 | 10/2007 | Lee |
| 2006/0217743 A1 | 9/2006 | Messerly et al. | | 2007/0250057 A1 | 10/2007 | Nobis et al. |
| 2006/0229639 A1 | 10/2006 | Whitfield | | 2007/0255096 A1 | 11/2007 | Stefanchik et al. |
| 2006/0229640 A1 | 10/2006 | Whitfield | | 2007/0255100 A1 | 11/2007 | Barlow et al. |
| 2006/0237022 A1 | 10/2006 | Chen et al. | | 2007/0255273 A1 | 11/2007 | Fernandez et al. |
| 2006/0237023 A1 | 10/2006 | Cox et al. | | 2007/0255303 A1 | 11/2007 | Bakos et al. |
| 2006/0241570 A1 | 10/2006 | Wilk | | 2007/0255306 A1 | 11/2007 | Conlon et al. |
| 2006/0247576 A1 | 11/2006 | Poncet | | 2007/0260112 A1 | 11/2007 | Rahmani |
| 2006/0247673 A1 | 11/2006 | Voegele et al. | | 2007/0260117 A1 | 11/2007 | Zwolinski et al. |
| 2006/0253004 A1 | 11/2006 | Frisch et al. | | 2007/0260121 A1 | 11/2007 | Bakos et al. |
| 2006/0253039 A1 | 11/2006 | McKenna et al. | | 2007/0260273 A1 | 11/2007 | Cropper et al. |
| 2006/0258907 A1 | 11/2006 | Stefanchik et al. | | 2007/0270629 A1 | 11/2007 | Charles |
| 2006/0258908 A1 | 11/2006 | Stefanchik et al. | | 2007/0270889 A1 | 11/2007 | Conlon et al. |
| 2006/0258910 A1 | 11/2006 | Stefanchik et al. | | 2007/0270895 A1 | 11/2007 | Nobis et al. |
| 2006/0258954 A1 | 11/2006 | Timberlake et al. | | 2007/0270907 A1 | 11/2007 | Stokes et al. |
| 2006/0258955 A1 | 11/2006 | Hoffman et al. | | 2007/0282371 A1 | 12/2007 | Lee et al. |
| 2006/0259010 A1 | 11/2006 | Stefanchik et al. | | 2007/0299387 A1 | 12/2007 | Williams et al. |
| 2006/0264752 A1 | 11/2006 | Rubinsky et al. | | 2008/0004650 A1 | 1/2008 | George |
| 2006/0264904 A1 | 11/2006 | Kerby et al. | | 2008/0015409 A1 | 1/2008 | Barlow et al. |
| 2006/0264930 A1 | 11/2006 | Nishimura | | 2008/0015552 A1 | 1/2008 | Doyle et al. |
| 2006/0270902 A1 | 11/2006 | Igarashi et al. | | 2008/0027387 A1 | 1/2008 | Grabinsky |
| 2006/0271102 A1 | 11/2006 | Bosshard et al. | | 2008/0033451 A1 | 2/2008 | Rieber et al. |
| 2006/0276835 A1 | 12/2006 | Uchida | | 2008/0051629 A1 | 2/2008 | Sugiyama et al. |
| 2006/0281970 A1 | 12/2006 | Stokes et al. | | 2008/0051735 A1 | 2/2008 | Measamer et al. |
| 2006/0282106 A1 | 12/2006 | Cole et al. | | 2008/0058586 A1 | 3/2008 | Karpiel |
| 2006/0285732 A1 | 12/2006 | Horn et al. | | 2008/0065169 A1 | 3/2008 | Colliou et al. |
| 2006/0287644 A1 | 12/2006 | Inganas et al. | | 2008/0071264 A1 | 3/2008 | Azure |
| 2006/0287666 A1 | 12/2006 | Saadat et al. | | 2008/0086172 A1 | 4/2008 | Martin et al. |
| 2006/0293626 A1 | 12/2006 | Byrum et al. | | 2008/0097472 A1 | 4/2008 | Agmon et al. |
| 2007/0002135 A1 | 1/2007 | Glukhovsky | | 2008/0097483 A1 | 4/2008 | Ortiz et al. |
| 2007/0005019 A1 | 1/2007 | Okishige | | 2008/0103527 A1 | 5/2008 | Martin et al. |
| 2007/0015965 A1 | 1/2007 | Cox et al. | | 2008/0114384 A1 | 5/2008 | Chang et al. |
| 2007/0016225 A1 | 1/2007 | Nakao | | 2008/0119870 A1 | 5/2008 | Williams |
| 2007/0032700 A1 | 2/2007 | Fowler et al. | | 2008/0125796 A1 | 5/2008 | Graham |
| 2007/0032701 A1 | 2/2007 | Fowler et al. | | 2008/0132892 A1 | 6/2008 | Lunsford et al. |
| 2007/0043261 A1 | 2/2007 | Watanabe et al. | | 2008/0139882 A1 | 6/2008 | Fujimori |
| 2007/0043345 A1 | 2/2007 | Davalos et al. | | 2008/0147113 A1 | 6/2008 | Nobis et al. |

| | | |
|---|---|---|
| 2008/0171907 A1 | 7/2008 | Long et al. |
| 2008/0188868 A1 | 8/2008 | Weitzner et al. |
| 2008/0200755 A1 | 8/2008 | Bakos |
| 2008/0200762 A1 | 8/2008 | Stokes et al. |
| 2008/0200911 A1 | 8/2008 | Long |
| 2008/0200912 A1 | 8/2008 | Long |
| 2008/0200933 A1 | 8/2008 | Bakos et al. |
| 2008/0200934 A1 | 8/2008 | Fox |
| 2008/0208213 A1 | 8/2008 | Benjamin et al. |
| 2008/0221587 A1 | 9/2008 | Schwartz |
| 2008/0221619 A1 | 9/2008 | Spivey et al. |
| 2008/0228213 A1 | 9/2008 | Blakeney et al. |
| 2008/0230972 A1 | 9/2008 | Ganley |
| 2008/0234696 A1 | 9/2008 | Taylor et al. |
| 2008/0243106 A1 | 10/2008 | Coe et al. |
| 2008/0243148 A1 | 10/2008 | Mikkaichi et al. |
| 2008/0243176 A1 | 10/2008 | Weitzner et al. |
| 2008/0262540 A1 | 10/2008 | Bangera et al. |
| 2008/0269782 A1 | 10/2008 | Stefanchik et al. |
| 2008/0269783 A1 | 10/2008 | Griffith |
| 2008/0275474 A1 | 11/2008 | Martin et al. |
| 2008/0275475 A1 | 11/2008 | Schwemberger et al. |
| 2008/0287737 A1 | 11/2008 | Dejima |
| 2008/0287983 A1 | 11/2008 | Smith et al. |
| 2008/0300461 A1 | 12/2008 | Shaw et al. |
| 2008/0300547 A1 | 12/2008 | Bakos |
| 2008/0309758 A1 | 12/2008 | Karasawa et al. |
| 2008/0312496 A1 | 12/2008 | Zwolinski |
| 2008/0312499 A1 | 12/2008 | Handa et al. |
| 2008/0312500 A1 | 12/2008 | Asada et al. |
| 2008/0312506 A1 | 12/2008 | Spivey et al. |
| 2008/0319436 A1 | 12/2008 | Daniel et al. |
| 2008/0319439 A1 | 12/2008 | Ootsubu |
| 2009/0054728 A1 | 2/2009 | Trusty |
| 2009/0062788 A1 | 3/2009 | Long et al. |
| 2009/0062792 A1 | 3/2009 | Vakharia et al. |
| 2009/0062795 A1 | 3/2009 | Vakharia et al. |
| 2009/0069634 A1 | 3/2009 | Larkin |
| 2009/0076499 A1 | 3/2009 | Azure |
| 2009/0082776 A1 | 3/2009 | Cresina |
| 2009/0082779 A1 | 3/2009 | Nakao |
| 2009/0112059 A1 | 4/2009 | Nobis |
| 2009/0112062 A1 | 4/2009 | Bakos |
| 2009/0112063 A1 | 4/2009 | Bakos et al. |
| 2009/0131751 A1 | 5/2009 | Spivey et al. |
| 2009/0131932 A1 | 5/2009 | Vakharia et al. |
| 2009/0131933 A1 | 5/2009 | Ghabrial et al. |
| 2009/0143639 A1 | 6/2009 | Stark |
| 2009/0143649 A1 | 6/2009 | Rossi |
| 2009/0143794 A1 | 6/2009 | Conlon et al. |
| 2009/0149710 A1 | 6/2009 | Stefanchik et al. |
| 2009/0177031 A1 | 7/2009 | Surti et al. |
| 2009/0177219 A1 | 7/2009 | Conlon |
| 2009/0182332 A1 | 7/2009 | Long et al. |
| 2009/0192344 A1 | 7/2009 | Bakos et al. |
| 2009/0198231 A1 | 8/2009 | Esser et al. |
| 2009/0227828 A1 | 9/2009 | Swain et al. |
| 2009/0248055 A1 | 10/2009 | Spivey et al. |
| 2009/0281559 A1 | 11/2009 | Swain et al. |
| 2009/0287236 A1 | 11/2009 | Bakos et al. |
| 2009/0292164 A1 | 11/2009 | Yamatani |
| 2009/0299135 A1 | 12/2009 | Spivey |
| 2009/0299143 A1 | 12/2009 | Conlon et al. |
| 2009/0299362 A1 | 12/2009 | Long et al. |
| 2009/0299385 A1 | 12/2009 | Stefanchik et al. |
| 2009/0299406 A1 | 12/2009 | Swain et al. |
| 2009/0299409 A1 | 12/2009 | Coe et al. |
| 2009/0306658 A1 | 12/2009 | Nobis et al. |
| 2009/0306683 A1 | 12/2009 | Zwolinski et al. |
| 2009/0322864 A1 | 12/2009 | Karasawa et al. |
| 2009/0326561 A1 | 12/2009 | Carroll, II et al. |
| 2010/0010294 A1 | 1/2010 | Conlon et al. |
| 2010/0010298 A1 | 1/2010 | Bakos et al. |
| 2010/0010299 A1 | 1/2010 | Bakos et al. |
| 2010/0010303 A1 | 1/2010 | Bakos |
| 2010/0010510 A1 | 1/2010 | Stefanchik |
| 2010/0010511 A1 | 1/2010 | Harris et al. |
| 2010/0023032 A1 | 1/2010 | Granja Filho |
| 2010/0042045 A1 | 2/2010 | Spivey |
| 2010/0048990 A1 | 2/2010 | Bakos |
| 2010/0049190 A1 | 2/2010 | Long et al. |
| 2010/0049223 A1 | 2/2010 | Granja Filho |
| 2010/0056861 A1 | 3/2010 | Spivey |
| 2010/0056862 A1 | 3/2010 | Bakos |
| 2010/0057085 A1 | 3/2010 | Holcomb et al. |
| 2010/0057108 A1 | 3/2010 | Spivey et al. |
| 2010/0076451 A1 | 3/2010 | Zwolinski et al. |
| 2010/0081877 A1 | 4/2010 | Vakharia |
| 2010/0087813 A1 | 4/2010 | Long |
| 2010/0113872 A1 | 5/2010 | Asada et al. |
| 2010/0121362 A1 | 5/2010 | Clague et al. |
| 2010/0130817 A1 | 5/2010 | Conlon |
| 2010/0130975 A1 | 5/2010 | Long |
| 2010/0131005 A1 | 5/2010 | Conlon |
| 2010/0152539 A1 | 6/2010 | Ghabrial et al. |
| 2010/0152609 A1 | 6/2010 | Zwolinski et al. |
| 2010/0152746 A1 | 6/2010 | Ceniccola et al. |
| 2010/0179510 A1 | 7/2010 | Fox et al. |
| 2010/0179530 A1 | 7/2010 | Long et al. |
| 2010/0191050 A1 | 7/2010 | Zwolinski |
| 2010/0191267 A1 | 7/2010 | Fox |
| 2010/0198005 A1 | 8/2010 | Fox |
| 2010/0198149 A1 | 8/2010 | Fox |
| 2010/0198244 A1 | 8/2010 | Spivey et al. |
| 2010/0198248 A1 | 8/2010 | Vakharia |
| 2010/0249700 A1 | 9/2010 | Spivey |
| 2010/0286791 A1 | 11/2010 | Goldsmith |
| 2010/0298642 A1 | 11/2010 | Trusty et al. |
| 2010/0312056 A1 | 12/2010 | Galperin et al. |
| 2010/0331622 A2 | 12/2010 | Conlon |
| 2010/0331774 A2 | 12/2010 | Spivey |
| 2011/0093009 A1 | 4/2011 | Fox |
| 2011/0098694 A1 | 4/2011 | Long |
| 2011/0098704 A1 | 4/2011 | Long et al. |
| 2011/0105850 A1 | 5/2011 | Voegele et al. |
| 2011/0112434 A1 | 5/2011 | Ghabrial et al. |
| 2011/0115891 A1 | 5/2011 | Trusty |
| 2011/0124964 A1 | 5/2011 | Nobis |
| 2011/0152609 A1 | 6/2011 | Trusty et al. |
| 2011/0152610 A1 | 6/2011 | Trusty et al. |
| 2011/0152612 A1 | 6/2011 | Trusty et al. |
| 2011/0152858 A1 | 6/2011 | Long et al. |
| 2011/0152859 A1 | 6/2011 | Long et al. |
| 2011/0152878 A1 | 6/2011 | Trusty et al. |
| 2011/0152923 A1 | 6/2011 | Fox |
| 2011/0160514 A1 | 6/2011 | Long et al. |
| 2011/0190659 A1 | 8/2011 | Long et al. |
| 2011/0190764 A1 | 8/2011 | Long et al. |

FOREIGN PATENT DOCUMENTS

| | | |
|---|---|---|
| DE | 3008120 A1 | 9/1980 |
| DE | 4323585 A1 | 1/1995 |
| DE | 19757056 B4 | 8/2008 |
| DE | 102006027873 B4 | 10/2009 |
| EP | 0086338 A1 | 8/1983 |
| EP | 0286415 A2 | 10/1988 |
| EP | 0589454 A2 | 3/1994 |
| EP | 0464479 B1 | 3/1995 |
| EP | 0529675 B1 | 2/1996 |
| EP | 0724863 B1 | 7/1999 |
| EP | 0760629 B1 | 11/1999 |
| EP | 0818974 B1 | 7/2001 |
| EP | 1281356 A2 | 2/2003 |
| EP | 0947166 B1 | 5/2003 |
| EP | 0836832 B1 | 12/2003 |
| EP | 1402837 A1 | 3/2004 |
| EP | 0744918 B1 | 4/2004 |
| EP | 0931515 B1 | 8/2004 |
| EP | 1411843 B1 | 10/2004 |
| EP | 1150614 B1 | 11/2004 |
| EP | 1477104 A1 | 11/2004 |
| EP | 1481642 A1 | 12/2004 |
| EP | 1493391 A1 | 1/2005 |
| EP | 0848598 B1 | 2/2005 |
| EP | 1281360 B1 | 3/2005 |
| EP | 1568330 A1 | 8/2005 |
| EP | 1452143 B1 | 9/2005 |
| EP | 1616527 A2 | 1/2006 |

| | | |
|---|---|---|
| EP | 1006888 B1 | 3/2006 |
| EP | 1629764 A1 | 3/2006 |
| EP | 1013229 B1 | 6/2006 |
| EP | 1721561 A1 | 11/2006 |
| EP | 1153578 B1 | 3/2007 |
| EP | 1334696 B1 | 3/2007 |
| EP | 1769766 A1 | 4/2007 |
| EP | 1836971 A2 | 9/2007 |
| EP | 1836980 A1 | 9/2007 |
| EP | 1854421 A2 | 11/2007 |
| EP | 1857061 A1 | 11/2007 |
| EP | 1875876 A1 | 1/2008 |
| EP | 1891881 A1 | 2/2008 |
| EP | 1902663 A1 | 3/2008 |
| EP | 1477106 B1 | 6/2008 |
| EP | 1949844 A1 | 7/2008 |
| EP | 1518499 B1 | 8/2008 |
| EP | 1709918 B1 | 10/2008 |
| EP | 1985226 A2 | 10/2008 |
| EP | 1994904 A1 | 11/2008 |
| EP | 1707130 B1 | 12/2008 |
| EP | 1769749 B1 | 11/2009 |
| FR | 2731610 A1 | 9/1996 |
| GB | 330629 A | 6/1930 |
| GB | 2335860 A | 10/1999 |
| GB | 2403909 A | 1/2005 |
| GB | 2421190 A | 6/2006 |
| GB | 2443261 A | 4/2008 |
| JP | 56-46674 | 4/1981 |
| JP | 8-29699 A | 2/1996 |
| JP | 2002-369791 A | 12/2002 |
| JP | 2003-088494 A | 3/2003 |
| JP | 2003-235852 A | 8/2003 |
| JP | 2004-33525 A | 2/2004 |
| JP | 2004-065745 A | 3/2004 |
| JP | 2005-121947 A | 5/2005 |
| JP | 2005-261514 A | 9/2005 |
| NL | 1021295 C2 | 2/2004 |
| SU | 194230 | 5/1967 |
| SU | 980703 | 12/1982 |
| WO | WO 84/01707 A1 | 5/1984 |
| WO | WO 92/13494 A1 | 8/1992 |
| WO | WO 93/10850 A1 | 6/1993 |
| WO | WO 93/20760 A1 | 10/1993 |
| WO | WO 93/20765 A1 | 10/1993 |
| WO | WO 95/09666 A1 | 4/1995 |
| WO | WO 96/22056 A1 | 7/1996 |
| WO | WO 96/27331 A1 | 9/1996 |
| WO | WO 96/39946 A1 | 12/1996 |
| WO | WO 97/12557 A1 | 4/1997 |
| WO | WO 98/01080 A1 | 1/1998 |
| WO | WO 99/09919 A1 | 3/1999 |
| WO | WO 99/17661 A1 | 4/1999 |
| WO | WO 99/30622 A2 | 6/1999 |
| WO | WO 00/35358 A1 | 6/2000 |
| WO | WO 01/10319 A1 | 2/2001 |
| WO | WO 01/41627 A2 | 6/2001 |
| WO | WO 01/58360 A2 | 8/2001 |
| WO | WO 02/11621 A1 | 2/2002 |
| WO | WO 02/34122 A2 | 5/2002 |
| WO | WO 02/094082 A2 | 11/2002 |
| WO | WO 03/045260 A1 | 6/2003 |
| WO | WO 03/047684 A2 | 6/2003 |
| WO | WO 03/059412 A2 | 7/2003 |
| WO | WO 03/078721 A2 | 9/2003 |
| WO | WO 03/082129 A2 | 10/2003 |
| WO | WO 2004/006789 A1 | 1/2004 |
| WO | WO 2004/028613 A2 | 4/2004 |
| WO | WO 2004/037123 A1 | 5/2004 |
| WO | WO 2004/052221 A1 | 6/2004 |
| WO | WO 2004/086984 A1 | 10/2004 |
| WO | WO 2005/009211 A2 | 2/2005 |
| WO | WO 2005/018467 A2 | 3/2005 |
| WO | WO 2005/037088 A2 | 4/2005 |
| WO | WO 2005/048827 A1 | 6/2005 |
| WO | WO 2005/065284 A2 | 7/2005 |
| WO | WO 2005/097019 A2 | 10/2005 |
| WO | WO 2005/097234 A2 | 10/2005 |
| WO | WO 2005/112810 A2 | 12/2005 |
| WO | WO 2005/120363 A1 | 12/2005 |
| WO | WO 2006/007399 A1 | 1/2006 |
| WO | WO 2006/041881 A2 | 4/2006 |
| WO | WO 2006/060405 A2 | 6/2006 |
| WO | WO 2006/110733 A2 | 10/2006 |
| WO | WO 2006/113216 A2 | 10/2006 |
| WO | WO 2007/014063 A2 | 2/2007 |
| WO | WO 2007/048085 A2 | 4/2007 |
| WO | WO 2007/063550 A2 | 6/2007 |
| WO | WO 2007/100067 A1 | 9/2007 |
| WO | WO 2007/109171 A2 | 9/2007 |
| WO | WO 2008/005433 A1 | 1/2008 |
| WO | WO 2008/041225 A2 | 4/2008 |
| WO | WO 2008/076337 A1 | 6/2008 |
| WO | WO 2008/076800 A2 | 6/2008 |
| WO | WO 2008/101075 A2 | 8/2008 |
| WO | WO 2008/102154 A2 | 8/2008 |
| WO | WO 2009/021030 A1 | 2/2009 |
| WO | WO 2009/027065 A1 | 3/2009 |
| WO | WO 2009/029065 A1 | 3/2009 |
| WO | WO 2009/032623 A2 | 3/2009 |
| WO | WO 2009/121017 A1 | 10/2009 |
| WO | WO 2010/027688 A1 | 3/2010 |
| WO | WO 2010/080974 A1 | 7/2010 |
| WO | WO 2010/088481 A1 | 8/2010 |

OTHER PUBLICATIONS

Ethicon, Inc., "Wound Closure Manual: Chapter 3 (The Surgical Needle)," 15 pages, (publication date unknown).

Guido M. Sclabas, M.D., et al., "Endoluminal Methods for Gastrotomy Closure in Natural Orifice TransEnteric Surgery (NOTES)," Surgical Innovation, vol. 13, No. 1, pp. 23-30, Mar. 2006.

Fritscher-Ravens, et al., "Transgastric Gastropexy and Hiatal Hernia Repair for GERD Under EUS Control: a Porcine Model," Gastrointestinal Endoscopy, vol. 59, No. 1, pp. 89-95, 2004.

Ogando, "Prototype Tools That Go With the Flow," Design News, 2 pages, Jul. 17, 2006.

Edd, et al., "In Vivo Results of a New Focal Tissue Ablation Technique: Irreversible Electroporation," IEEE Trans Biomed Eng, vol. 53, pp. 1409-1415, 2006.

Kennedy, et al., "High-Burst-Strength, Feedback-Controlled Bipolar Vessel Sealing," Surgical Endoscopy, vol. 12, pp. 876-878 (1998).

Collins et al., "Local Gene Therapy of Solid Tumors with GM-CSF and B7-1 Eradicates Both Treated and Distal Tumors," Cancer Gene Therapy, vol. 13, pp. 1061-1071 (2006).

K. Sumiyama et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).

K. Sumiyama et al., "Submucosal Endoscopy with Mucosal Flap Safety Valve," Gastrointest Endosc. Apr. 2007, vol. 65(4) pp. 694-695 (Abstract).

K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).

K. Sumiyama et al., "Endoscopic Caps," Tech. Gastrointest. Endosc., vol. 8, pp. 28-32, 2006.

"Z-Offset Technique Used in the Introduction of Trocar During Laparoscopic Surgery," M.S. Hershey NOTES Presentation to EES NOTES Development Team, Sep. 27, 2007.

F.N. Denans, Nouveau Procede Pour La Guerison Des Plaies Des Intestines. Extrait Des Seances De La Societe Royale De Medecine De Marseille, Pendant Le Mois De Dec. 1825, et le Premier Tremestre De 1826, Séance Du Feb. 24, 1826. Recueil De La Societe Royale De Medecin De Marseille. Marseille: Impr. D'Achard, 1826; 1:127-31. (with English translation).

I. Fraser, "An Historical Perspective on Mechanical Aids in Intestinal Anastamosis," Surg. Gynecol. Obstet. (Oct. 1982), vol. 155, pp. 566-574.

M.E. Ryan et al., "Endoscopic Intervention for Biliary Leaks After Laparoscopic Cholecystectomy: A Multicenter Review," Gastrointest. Endosc., vol. 47(3), 1998, pp. 261-266.

C. Cope, "Creation of Compression Gastroenterostomy by Means of the Oral, Percutaneous, or Surgical Introduction of Magnets: Feasibility Study in Swine," J. Vasc Interv Radio!, (1995), vol. 6(4), pp. 539-545.

J.W. Hazey et al., "Natural Orifice Transgastric Endoscopic Peritoneoscopy in Humans: Initial Clinical Trial," Surg Endosc, (Jan. 2008), vol. 22(1), pp. 16-20.

N. Chopita et al., "Endoscopic Gastroenteric Anastamosis Using Magnets," Endoscopy, (2005), vol. 37(4), pp. 313-317.

C. Cope et al., "Long Term Patency of Experimental Magnetic Compression Gastroenteric Anastomoses Achieved with Covered Stents," Gastrointest Endosc, (2001), vol. 53, pp. 780-784.

H. Okajima et al., "Magnet Compression Anastamosis for Bile Duct Stenosis After Duct to Duct Biliary Reconstruction in Living Donor Liver Transplantation," Liver Transplantation (2005), pp. 473-475.

A. Fritscher-Ravens et al., "Transluminal Endosurgery: Single Lumen Access Anastamotic Device for Flexible Endoscopy," Gastrointestinal Endosc, (2003), vol. 58(4), pp. 585-591.

G.A. Hallenbeck, M.D. et al., "An Instrument for Colorectal Anastomosis Without Sutrues," Dis Col Rectum, (1963), vol. 5, pp. 98-101.

T. Hardy, Jr., M.D. et al., "A Biofragmentable Ring for Sutureless Bowel Anastomosis. An Experimental Study," Dis Col Rectum, (1985), vol. 28, pp. 484-490.

P. O'Neill, M.D. et al., "Nonsuture Intestinal Anastomosis," Am J. Surg, (1962), vol. 104, pp. 761-767.

C.P. Swain, M.D. et al., "Anastomosis at Flexible Endoscopy: An Experimental Study of Compression Button Gastrojejunostomy," Gastrointest Endosc, (1991), vol. 37, pp. 628-632.

J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.

USGI® EndoSurgical Operating System—g-Prox® Tissue Grasper/Approximation Device; [online] URL: http://www.usgimedicalcom/eos/components-gprox.htm—accessed May 30, 2008 (2 pages).

Printout of web page—http://www.vacumed.com/zcom/product/Product.do?compid=27&prodid=852, #51XX Low-Cost Permanent Tubes 2MM ID, Smooth Interior Walls, VacuMed, Ventura, California, Accessed Jul. 24, 2007.

Endoscopic Retrograde Cholangiopancreatogram (ERCP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).

ERCP; Jackson Siegelbaum Gastroenterology; [online] URL: http://www.gicare.com/pated/epdgs20.htm; accessed Feb. 21, 2008 (3 pages).

D.G. Fong et al., "Transcolonic Ventral Wall Hernia Mesh Fixation in a Porcine Model," Endoscopy 2007; 39: 865-869.

B. Rubinsky, Ph.D., "Irreversible Electroporation in Medicine," Technology in Cancer Research and Treatment, vol. 6, No. 4, Aug. 2007, pp. 255-259.

D.B. Nelson, MD et al., "Endoscopic Hemostatic Devices," Gastrointestinal Endoscopy, vol. 54, No. 6, 2001, pp. 833-840.

CRE™ Pulmonary Balloon Dilator; [online] URL: http://www.bostonscientific.com/Device.bsci?page=HCP_Overview&navRelId=1000.1003&method=D..., accessed Jul. 18, 2008 (4 pages).

U.S. Appl. No. 11/744,271, filed May 4, 2007.
U.S. Appl. No. 11/744,279, filed May 4, 2007.
U.S. Appl. No. 11/796,035, filed Apr. 26, 2007.
U.S. Appl. No. 11/796,357, filed Apr. 27, 2007.
U.S. Appl. No. 11/894,358, filed Aug. 21, 2007.
U.S. Appl. No. 11/897,676, filed Aug. 31, 2007.
U.S. Appl. No. 11/968,810, filed Jan. 3, 2008.
U.S. Appl. No. 11/981,070, filed Oct. 31, 2007.
U.S. Appl. No. 11/981,078, filed Oct. 31, 2007.
U.S. Appl. No. 11/981,134, filed Oct. 31, 2007.
U.S. Appl. No. 11/986,084, filed Nov. 20, 2007.
U.S. Appl. No. 11/986,420, filed Nov. 21, 2007.
U.S. Appl. No. 11/986,489, filed Nov. 21, 2007.
U.S. Appl. No. 11/998,370, filed Nov. 29, 2007.
U.S. Appl. No. 12/014,417, filed Jan. 5, 2008.
U.S. Appl. No. 12/019,461, filed Jan. 24, 2008.
U.S. Appl. No. 12/045,318, filed Mar. 10, 2008.
U.S. Appl. No. 12/109,673, filed Apr. 25, 2008.
U.S. Appl. No. 12/109,699, filed Apr. 25, 2008.
U.S. Appl. No. 12/115,916, filed May 6, 2008.
U.S. Appl. No. 12/122,031, filed May 16, 2008.
U.S. Appl. No. 12/129,784, filed May 30, 2008.
U.S. Appl. No. 12/129,880, filed May 30, 2008.
U.S. Appl. No. 12/130,010, filed May 30, 2008.
U.S. Appl. No. 12/130,023, filed May 30, 2008.
U.S. Appl. No. 12/130,224, filed May 30, 2008.
U.S. Appl. No. 12/130,652, filed May 30, 2008.
U.S. Appl. No. 12/133,109, filed Jun. 4, 2008.
U.S. Appl. No. 12/133,953, filed Jun. 5, 2008.
U.S. Appl. No. 12/163,255, filed Jun. 27, 2008.
U.S. Appl. No. 12/169,868, filed Jul. 9, 2008.
U.S. Appl. No. 12/170,862, filed Jul. 10, 2008.
U.S. Appl. No. 12/172,752, filed Jul. 14, 2008.
U.S. Appl. No. 12/172,766, filed Jul. 14, 2008.
U.S. Appl. No. 12/172,782, filed Jul. 14, 2008.
U.S. Appl. No. 11/762,855, filed Jun. 14, 2007.
U.S. Appl. No. 12/192,372, filed Aug. 15, 2008.
U.S. Appl. No. 12/203,330, filed Sep. 3, 2008.
U.S. Appl. No. 12/197,749, filed Aug. 25, 2008.
U.S. Appl. No. 12/197,653, filed Aug. 25, 2008.
U.S. Appl. No. 12/202,740, filed Sep. 2, 2008.
U.S. Appl. No. 12/203,458, filed Sep. 3, 2008.
U.S. Appl. No. 12/201,812, filed Aug. 29, 2008.
U.S. Appl. No. 12/243,334, filed Oct. 1, 2008.
U.S. Appl. No. 12/234,425, filed Sep. 19, 2008.
U.S. Appl. No. 11/756,914, filed Jun. 1, 2007.
U.S. Appl. No. 12/060,601, filed Apr. 1, 2008.

International Search Report for PCT/US2009/055680, Dec. 14, 2009 (8 pages).

J.D. Paulson, M.D., et al., "Development of Flexible Culdoscopy," The Journal of the American Association of Gynecologic Laparoscopists, Nov. 1999, vol. 6, No. 4, pp. 487-490.

H. Seifert, et al., "Retroperitoneal Endoscopic Debridement for Infected Peripancreatic Necrosis," The Lancet, Research Letters, vol. 356, Aug. 19, 2000, pp. 653-655.

K.E. Mönkemüller, M.D., et al., "Transmural Drainage of Pancreatic Fluid Collections Without Electrocautery Using the Seldinger Technique," Gastrointestinal Endoscopy, vol. 48, No. 2, 1998, pp. 195-200, (Accepted Mar. 31, 1998).

D. Wilhelm et al., "An Innovative, Safe and Sterile Sigmoid Access (ISSA) for NOTES," Endoscopy 2007, vol. 39, pp. 401-406.

Nakazawa et al., "Radiofrequency Ablation of Hepatocellular Carcinoma: Correlation Between Local Tumor Progression After Ablation and Ablative Margin," AJR, 188, pp. 480-488 (Feb. 2007).

Miklavčič et al., "A validated model of in vivo electric field distribution in tissues for electrochemotherapy and for DNA electrotransfer for gene therapy," Biochimica et Biophysics Acta, 1523, pp. 73-83 (2000).

Evans, "Ablative and catheter-delivered therapies for colorectal liver metastases (CRLM)," EJSO, 33, pp. S64-S75 (2007).

Wong et al., "Combined Percutaneous Radiofrequency Ablation and Ethanol Injection for Hepatocellular Carcinoma in High-Risk Locations," AJR, 190, pp. W187-W195 (2008).

Heller et al., "Electrically mediated plasmid DNA delivery to hepatocellular carcinomas in vivo," Gene Therapy, 7, pp. 826-829 (2000).

Widera et al., "Increased DNA Vaccine Delivery and Immunogenicity by Electroporation in Vivo," The Journal of Immunology, 164, pp. 4635-4640 (2000).

Weaver et al., "Theory of electroporation: A review," Bioelectrochemistry and Bioenergetics, 41, pp. 135-160 (1996).

Mulier et al., "Radiofrequency Ablation Versus Resection for Resectable Colorectal Liver Metastases: Time for a Randomized Trial?" Annals of Surgical Oncology, 15(1), pp. 144-157 (2008).

Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).

Guyton at al., "Membrane Potentials and Action Potentials," W.B. Sanders, ed. Textbook of Medical Physiology, p. 56 (2000).
Guyton et al., "Contraction of Skeletal Muscle," Textbook of Medical Physiology, pp. 82-84 (2000).
"Ethicon Endo-Surgery Novel Investigational Notes and SSL Devices Featured in 15 Presentations at Sages," Apr. 22, 2009 Press Release; URL http://www.jnj.com/connect/news/all/20090422_152000; accessed Aug. 28, 2009 (3 pages).
"Ethicon Endo-Surgery Studies Presented At DDW Demonstrate Potential of Pure NOTES Surgery With Company's Toolbox," Jun. 3, 2009 Press Release; URL http://www.jnj.com/connect/news/product/20090603_120000; accessed Aug. 28, 2009 (3 pages).
Castellvi et al., "Hybrid Transvaginal NOTES Sleeve Gastrectomy in a Porcine Model Using a Magnetically Anchored Camera and Novel Instrumentation," Abstract submitted along with Poster at SAGES Annual Meeting in Phoenix, AZ, Apr. 22, 2009 (1 page).
OCTO Port Modular Laparoscopy System for Single Incision Access, Jan. 4, 2010; URL http://www.medgadget.com/archives/2010/01/octo_port_modular_laparo...; accessed Jan. 5, 2010 (4 pages).
Hakko Retractors, obtained Aug. 25, 2009 (5 pages).
Zadno at al., "Linear Superelasticity in Cold-Worked NI-TI," Engineering Aspects of Shape Memory Alloys, pp. 414-419.
U.S. Appl. No. 12/277,975, filed Nov. 25, 2008.
U.S. Appl. No. 12/277,957, filed Nov. 25, 2008.
U.S. Appl. No. 12/332,938, filed Dec. 11, 2008.
U.S. Appl. No. 12/337,340, filed Dec. 17, 2008.
U.S. Appl. No. 12/352,451, filed Jan. 12, 2009.
U.S. Appl. No. 12/359,824, filed Jan. 26, 2009.
U.S. Appl. No. 12/352,375, filed Jan. 12, 2009.
U.S. Appl. No. 12/359,053, filed Jan. 23, 2009.
U.S. Appl. No. 12/362,826, filed Jan. 30, 2009.
U.S. Appl. No. 12/363,137, filed Jan. 30, 2009.
U.S. Appl. No. 12/364,172, filed Feb. 2, 2009.
U.S. Appl. No. 12/364,256, filed Feb. 2, 2009.
U.S. Appl. No. 12/413,479, filed Mar. 27, 2009.
U.S. Appl. No. 12/468,462, filed May 19, 2009.
U.S. Appl. No. 12/607,252, filed Oct. 28, 2009.
U.S. Appl. No. 12/580,400, filed Oct. 16, 2009.
U.S. Appl. No. 12/607,388, filed Oct. 28, 2009.
U.S. Appl. No. 12/612,911, filed Nov. 5, 2009.
U.S. Appl. No. 12/614,143, filed Nov. 6, 2009.
U.S. Appl. No. 12/617,998, filed Nov. 13, 2009.
U.S. Appl. No. 12/640,440, filed Dec. 17, 2009.
U.S. Appl. No. 12/640,469, filed Dec. 17, 2009.
U.S. Appl. No. 12/640,476, filed Dec. 17, 2009.
U.S. Appl. No. 12/640,492, filed Dec. 17, 2009.
U.S. Appl. No. 12/641,823, filed Dec. 18, 2009.
U.S. Appl. No. 12/641,853, filed Dec. 18, 2009.
U.S. Appl. No. 12/641,837, filed Dec. 18, 2009.
U.S. Appl. No, 12/651,181, filed Dec. 31, 2009.
U.S. Appl. No. 12/696,598, filed Jan. 29, 2010.
U.S. Appl. No. 12/696,626, filed Jan. 29, 2010.
U.S. Appl. No. 12/694,452, filed Jan. 27, 2010.
U.S. Appl. No. 12/752,701, filed Apr. 1, 2010.
U.S. Appl. No. 13/013,131, filed Jan. 25, 2011.
U.S. Appl. No. 13/013,147, filed Jan. 25, 2011.
U.S. Appl. No. 12/900,132, filed Oct. 7, 2010.
U.S. Appl. No. 12/939,441, filed Nov. 4, 2010.
U.S. Appl. No. 12/902,531, filed Oct. 12, 2010.
U.S. Appl. No. 12/902,550, filed Oct. 12, 2010.
Written Opinion for PCT/US2009/055680, Dec. 14, 2009 (8 pages).
Zadno et al., "Linear Superelasticity in Cold-Worked NI-TI," Engineering Aspects of Shape Memory Alloys, pp. 414-419 (1990).

* cited by examiner

SURGICAL GRASPING DEVICE

BACKGROUND

Various embodiments are directed to surgical grasping devices and methods of using the same.

Minimally invasive procedures are desirable because such procedures can reduce pain and provide relatively quick recovery times as compared to conventional open medical procedures. Many minimally invasive procedures are performed with an endoscope (including without limitation laparoscopes). Such procedures permit a physician to position, manipulate, and view medical instruments and accessories inside the patient through a small access opening in the patient's body. Laparoscopy is a term used to describe such an "endosurgical" approach using an endoscope (often a rigid laparoscope). In this type of procedure, accessory devices are often inserted into a patient through trocars placed through the body wall. Still less invasive treatments include those that are performed through insertion of an endoscope through a natural body orifice to a treatment region. Examples of this approach include, but are not limited to, cystoscopy, hysteroscopy, esophagogastroduodenoscopy, and colonoscopy.

Many of these procedures employ a flexible endoscope during the procedure. Flexible endoscopes often have a flexible, steerable articulating section near the distal end that can be controlled by the clinician by utilizing controls at the proximal end. Some flexible endoscopes are relatively small (1 mm to 3 mm in diameter), and may have no integral accessory channel (also called biopsy channels or working channels). Other flexible endoscopes, including gastroscopes and colonoscopes, have integral working channels having a diameter of about 2.0 to 3.7 mm for the purpose of introducing and removing medical devices and other accessory devices to perform diagnosis or therapy within the patient. Certain specialized endoscopes are available, such as large working channel endoscopes having a working channel of 5 mm in diameter, which can be used to pass relatively large accessories, or to provide capability to suction large blood clots. Other specialized endoscopes include those having two or more working channels.

FIGURES

The novel features of the various embodiments are set forth with particularity in the appended claims. The various embodiments, however, both as to organization and methods of operation, together with advantages thereof, may best be understood by reference to the following description, taken in conjunction with the accompanying drawings as follows.

DESCRIPTION

Various embodiments may be directed to a surgical grasping device that may be used, for example, to position a distal portion of an endoscope. The surgical grasping device may comprise a grasping head, an optionally removable hollow shaft, and a translating member. The translating member may be coupled to the grasping head and may extend through the hollow shaft. The grasping head may be transitioned from an open position to a closed position when a clinician exerts a proximally directed force on the translating member. Likewise, the grasping head may be transitioned from the closed position to the open position when the clinician exerts a subsequent proximally directed force on the translating member.

The grasping device may be used for various purposes including, for example, to position the distal portion of an endoscope. In this use, the grasping device may be extended through a working channel of the endoscope, where it may contact and grip tissue. The clinician may then articulate the distal portion of the endoscope, using the grasping device as an anchor to control the movement of the distal portion. According to various embodiments, the hollow shaft may be removed proximally from the working channel leaving the grasping head gripping the tissue and the translating member extending though the working channel. This may give the distal portion of the end effector a greater range of motion relative to the grasping head, and may also allow other surgical instruments (e.g., scissors, cautery knives, suturing devices, etc.) to operate through the same working channel as the translating member.

Figure 1:
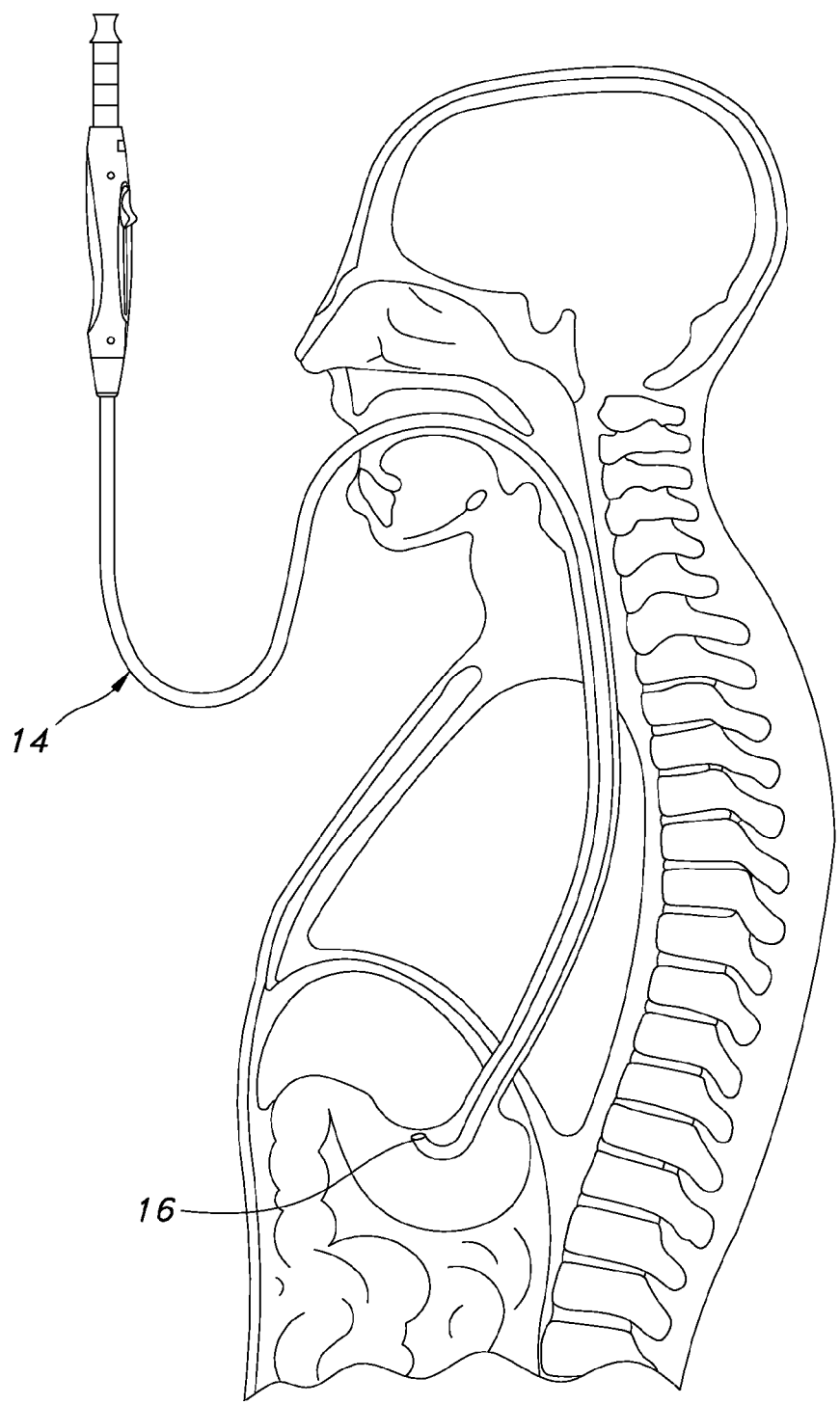
FIG. 1 illustrates one embodiment of an endoscope (illustrated here as a gastroscope) inserted into the upper gastrointestinal tract of a patient.

FIG. 1 illustrates one embodiment of an endoscope 14 (illustrated here as a gastroscope) inserted into the upper gastrointestinal tract of a patient. The endoscope 14 has a distal end 16 that may include various optical channels, illumination channels, and working channels. According to various embodiments, the endoscope 14 may be a flexible endoscope, may be introduced via natural orifices.

In one embodiment, Natural Orifice Translumenal Endoscopic Surgery (NOTES)™ techniques may be employed to introduce the endoscope 14 and various instruments into the patient and carry out the various procedures described herein. A NOTES™ technique is a minimally invasive therapeutic procedure that may be employed to treat diseased tissue or perform other therapeutic operations through a natural opening of the patient without making incisions in the abdomen. A natural opening may be the mouth, anus, and/or vagina.

Medical implantable instruments may be introduced into the patient to the target area via the natural opening. In a NOTES™ technique, a clinician inserts a flexible endoscope into one or more natural openings of the patient to view the target area, for example, using a camera. During endoscopic surgery, the clinician inserts surgical devices through one or more lumens or working channels of the endoscope 14 to perform various key surgical activities (KSA). These KSAs include forming an anastomosis between organs, repairing ulcers and other wounds, etc. Although the devices and methods described herein may be used with NOTES™ techniques, it will be appreciated that they may also be used with other surgical techniques including, for example, other endoscopic techniques, laparoscopic techniques, etc.

Figure 2:
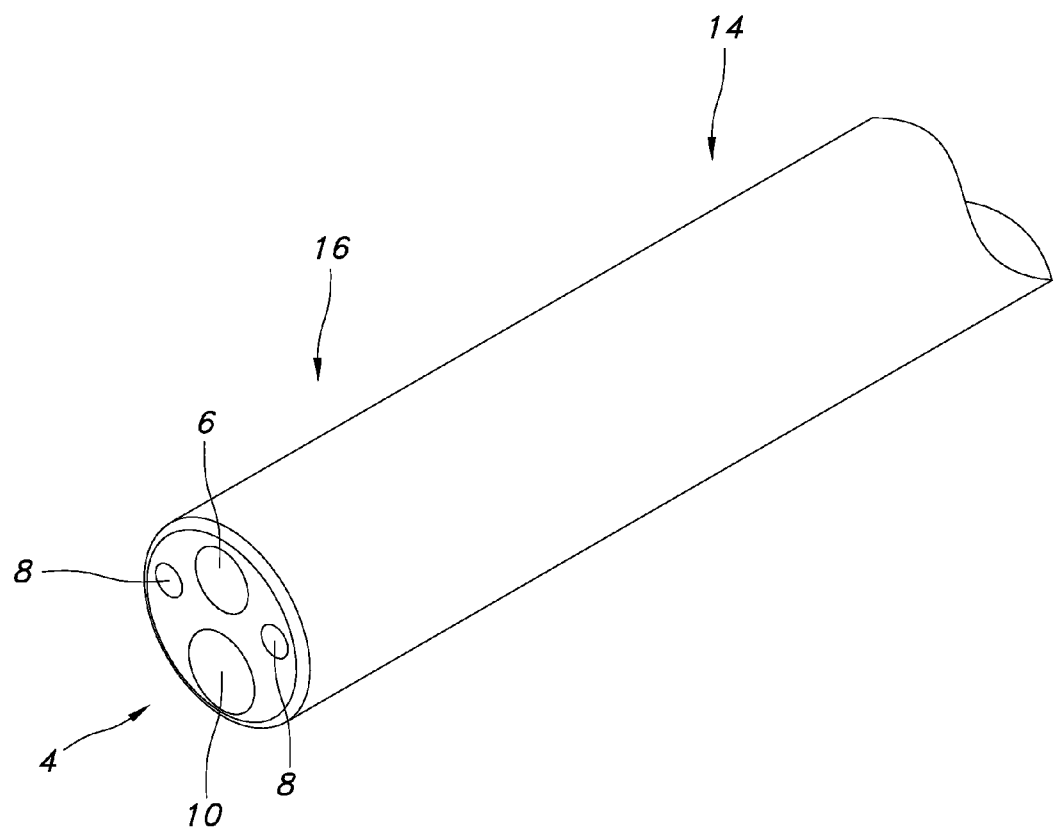
FIG. 2 illustrates one embodiment of a distal portion of the endoscope shown in FIG. 1.

FIG. 2 illustrates one embodiment of a distal portion 16 of the endoscope 14, which may be used with the grasping device described herein. The example endoscope 14 shown comprises a distal face 4, which defines the distal ends of illumination channels 8, an optical channel 6 and a working channel 10. The illumination channels 8 may comprise one or more optical fibers or other suitable waveguides for directing light from a proximally positioned light source (not shown) to the surgical site. The optical channel 6 may comprise one or more optical fibers or other suitable waveguides for receiving and transmitting an image of the surgical site proximally to a position where the image may be viewed by the clinician operating the endoscope 14. As described above, the working channel 10 may allow the clinician to introduce one or more surgical tools to the surgical site. Examples of such surgical tools include scissors, cautery knives, suturing devices, etc. It will be appreciated that the endoscope 14 is but one example of an endoscope that may be used in accordance with various embodiments. Endoscopes having alternate configurations of optical channels 6, illumination channels 8 and/or working channels 10 may also be used.

Figure 3:
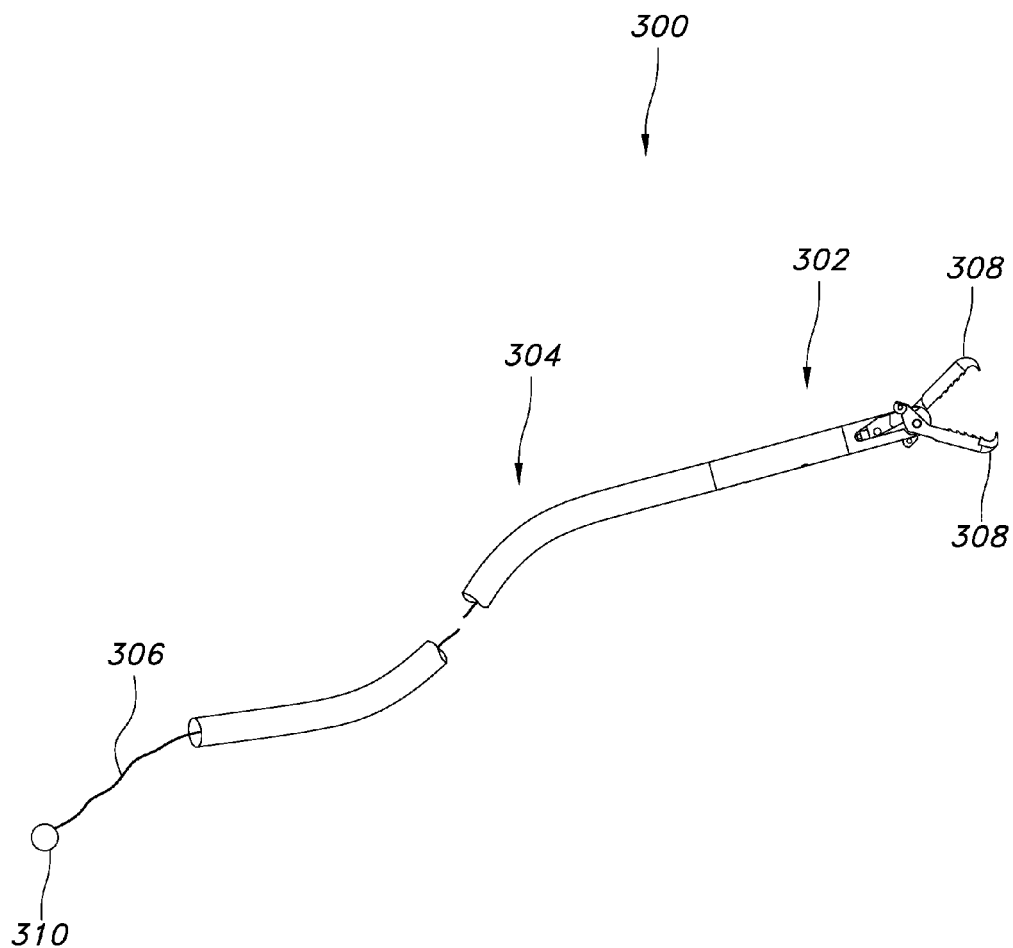
FIG. 3 illustrates one embodiment of a grasping device.

FIG. 3 illustrates one embodiment of a grasping device 300. The grasping device 300 may comprise a grasping head 302, a hollow shaft 304 and a translating member 306. The grasping head 302 may comprise a pair of jaw members 308 that may transition from the open position shown in FIG. 3 to a closed position. The jaw members 308 may be of any suitable shape and, according to various embodiments, may comprise teeth or other gripping features to increase friction between the jaw members 308 and tissue. The jaw members 308 may be transitioned from the open position to the closed position by exerting a proximally directed force on the translating member 306. The jaw members 308 may be transitioned back to the open position by exerting a subsequent proximally directed force on the translating member 306. The translating member 306 may be made from any suitable material, and in various embodiments may be a cable or wire. Also, the translating member 306 may comprise a handle 310 positioned proximally to allow the clinician to grip the translating member 306. Although the grasping device 300 is described herein for use in positioning the distal portion 16 of the endoscope 14, it will be appreciated that the grasping device 300 may be used in any other suitable surgical setting.

FIGS. 4A-4E illustrate embodiments of a process for using the grasping device 300 to position the distal portion 16 of the endoscope 14. The endoscope 14 may be provided to the surgical site according to any suitable technique including, for example a NOTES™ technique, another endoscopic technique, a laparoscopic technique, etc. In FIGS. 4A-4E, the endoscope 14 is provided to the surgical site via a lumen 402. For example, the clinician may introduce the endoscope 14 to the lumen 402 directly or indirectly via a natural orifice. The lumen 402 may be any accessible body lumen including, for example, the stomach, the small intestine, the duodenum, the large intestine, the bladder, the colon, etc. Once in the lumen 402, the clinician may provide a surgical tool (e.g., via the working channel 10) to make an opening 404 in the lumen 402. The distal portion 16 of the endoscope 14 may then be pushed through the opening 404 to access a cavity 400.

Figure 4A:
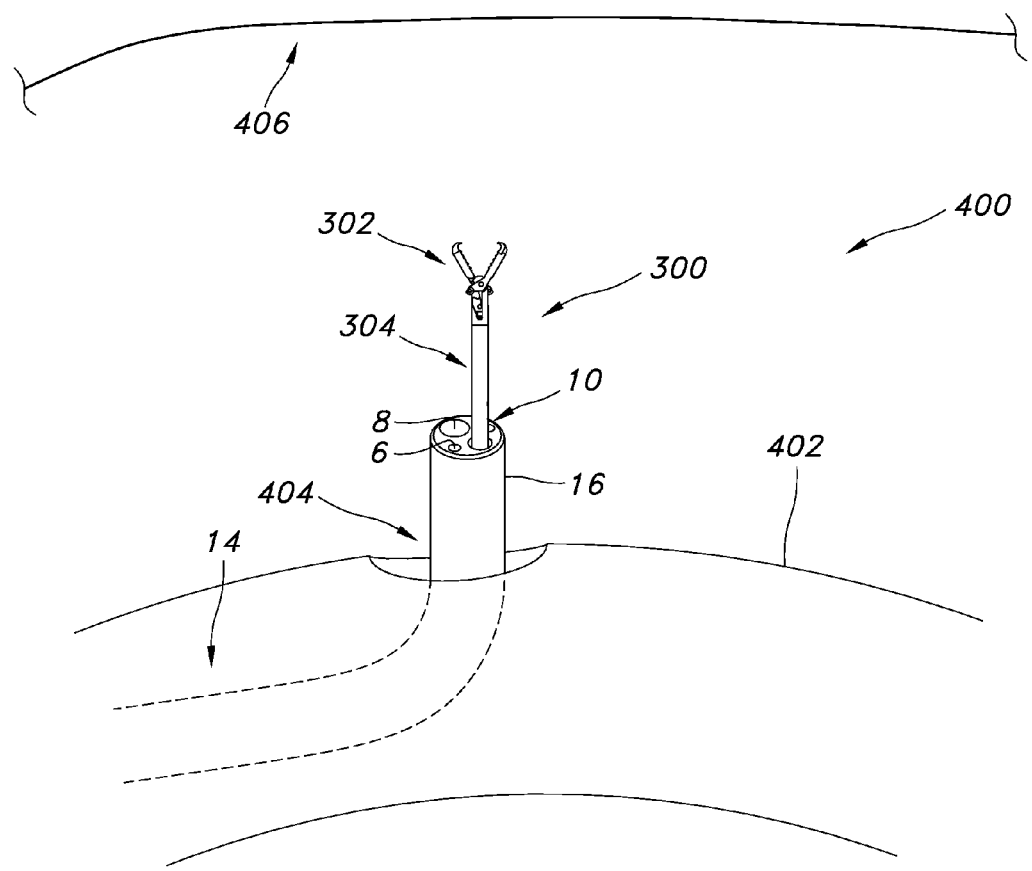
FIGS. 4A-4E illustrate embodiments of a process for using the grasping device of FIG. 3 to position the distal portion of the endoscope shown in FIG. 1.
Figure 4B:
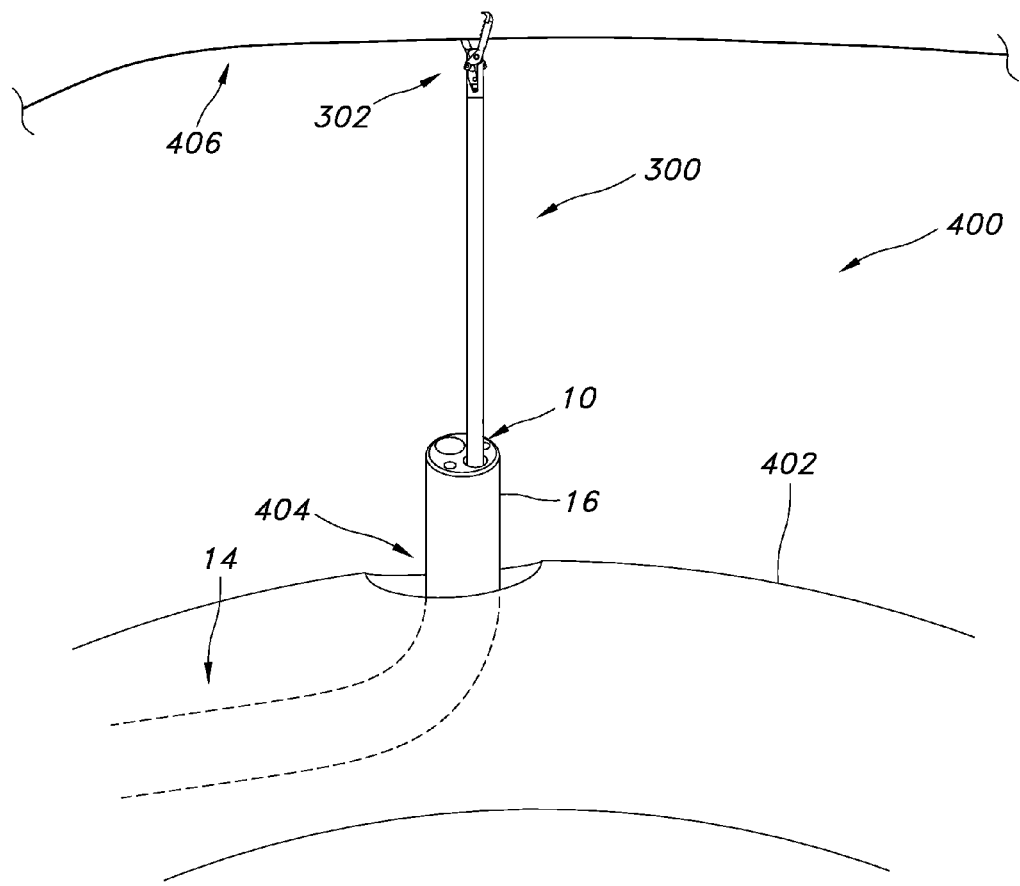

FIG. 4A illustrates one embodiment of the distal portion 16 of the endoscope 14 extending through the opening 404. The grasping device 300 is shown extending from the working channel 10 toward tissue 406. The tissue 406 may be any sort of tissue that the grasping device 300 may grip. For example, the tissue 406 may be tissue marking a boundary between body cavities such as, for example, the peritoneum or the diaphragm. In FIG. 4B, the grasping device 300 is shown extended to and grasping the tissue 406. This may allow the clinician to pull the distal portion 16 of the endoscope 14 towards the tissue 406. For example, the clinician may push the endoscope 14 distally while maintaining the grasping device 300 in a stationary position and/or pulling it proximally.

Figure 4C:
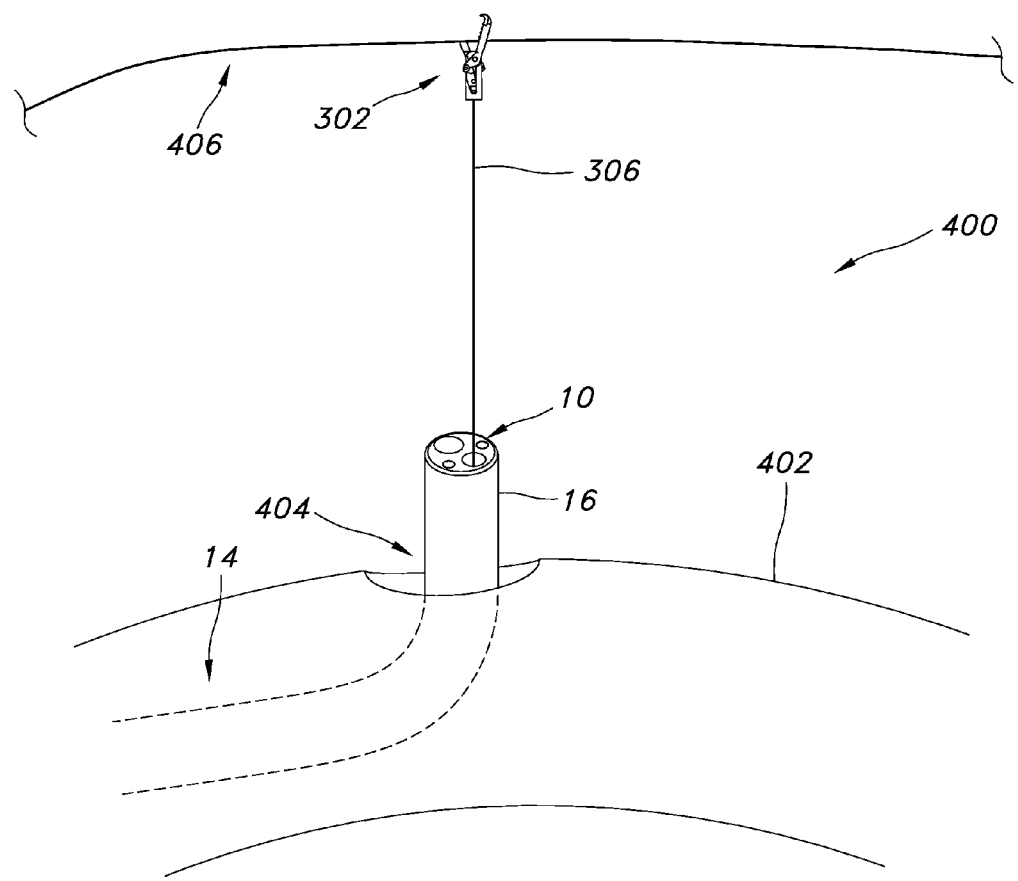
Figure 4D:
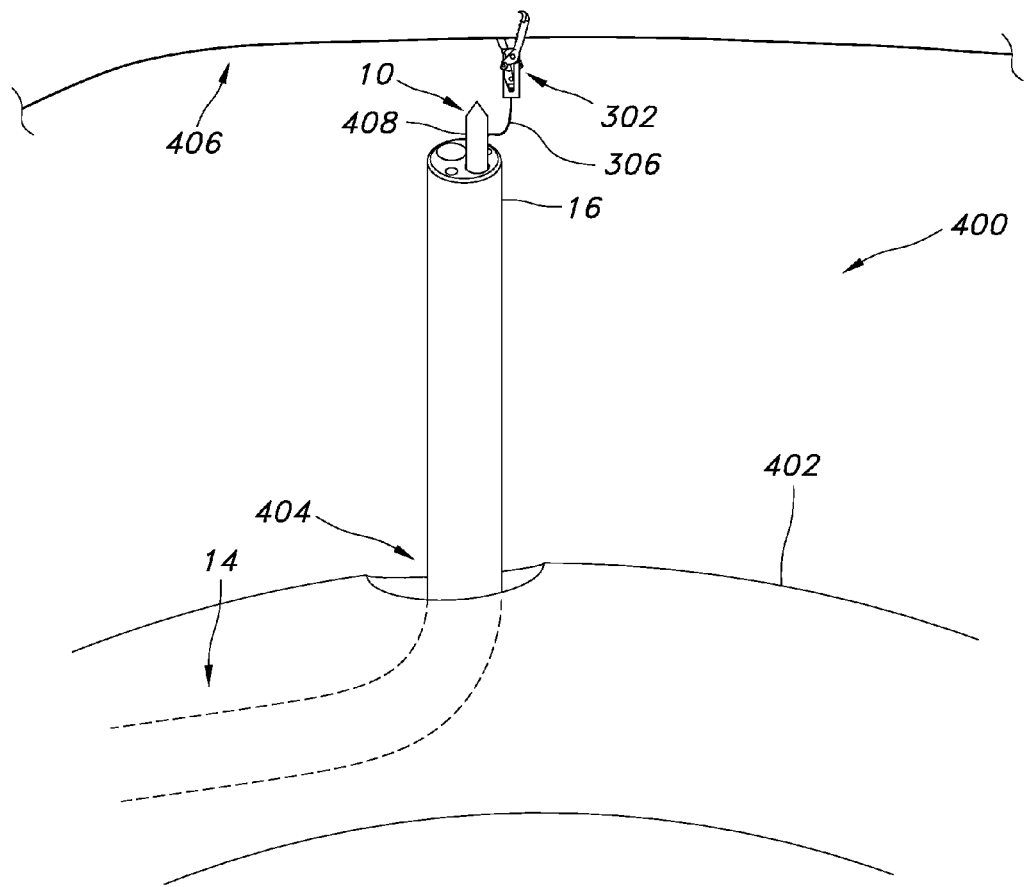

According to various embodiments, the hollow shaft 304 may be removed proximally through the working channel 10, the results of which are shown in FIG. 4C. Afterwards, the grasping head 302 may continue to grip the tissue 406, with the translating member 306 extending proximally from the grasping head 302 through the working channel 10. The translating member 306 may be small enough to allow other surgical tools, such as the needle 408 shown in FIG. 4D, to operate through the same working channel 10. In this way, the grasping device 300 may anchor the endoscope 14 to the tissue 406 while other surgical tools act on the tissue 406 and/or other tissue at the surgical site.

Figure 4E:
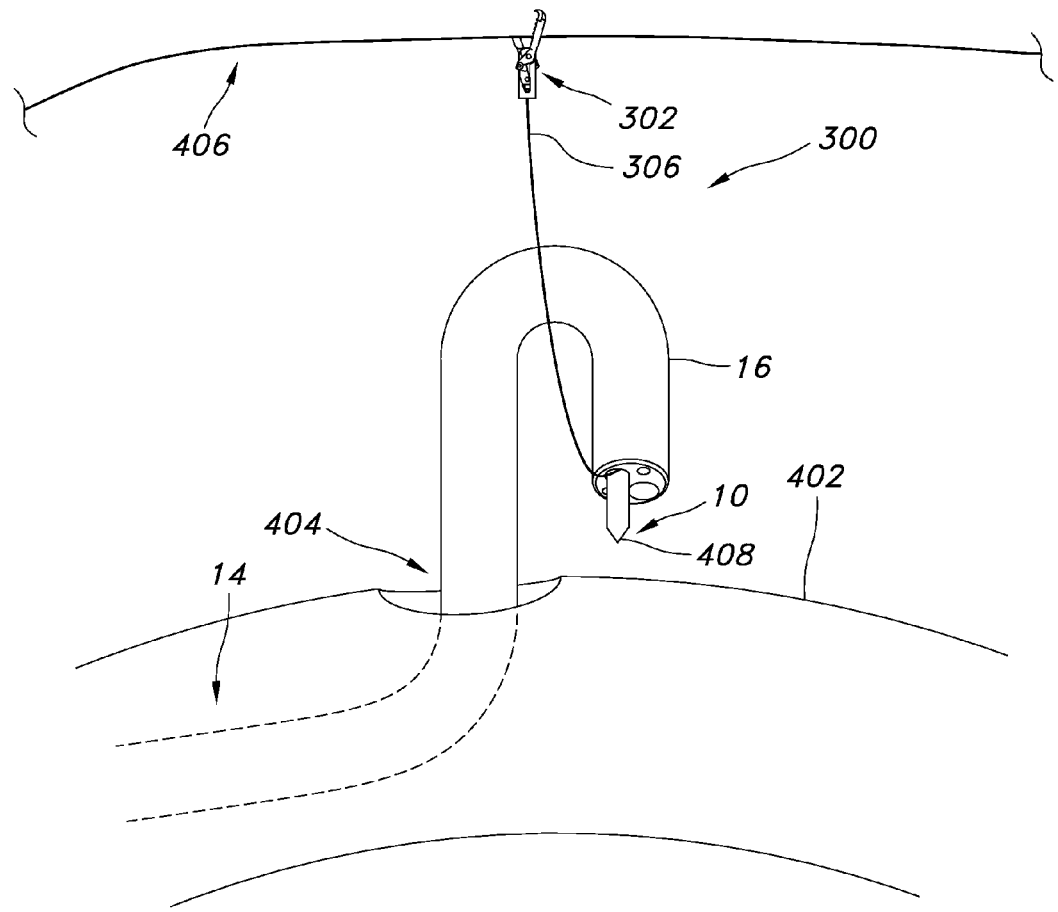

While anchored to the tissue 406, the endoscope 14 may be maneuvered in various ways. For example, the distal portion 16 of the endoscope 14 may be moved towards the tissue 406 as described above. Also, for example, FIG. 4E illustrates one embodiment of the distal portion 16 of the endoscope 14 after the endoscope has been articulated approximately 180° to face the lumen 402. During these and other articulating maneuvers, the grasping device 300 may serve as an anchor keeping the position of the distal portion 16 of the endoscope 14 substantially constant relative to the tissue 406. This may allow the clinician to more accurately position the endoscope 14. It will be appreciated that the clinician may maneuver the endoscope 14 before and/or after the hollow shaft 304 is removed. For example, with the hollow shaft 304 in place, the clinician may be able to perform techniques that require placing a large proximally directed force on the grasping device 300. In these situations, the hollow shaft 304 may prevent the jaw members 308 from opening or otherwise disengaging in response to the proximally directed force. In some embodiments, however, the degree of proximally directed force necessary to open the jaw members 308 may be more than is normally required to maneuver the endoscope 14. This may allow the clinician to maneuver the endoscope 14 after the hollow shaft 304 has been removed.

Figure 5:
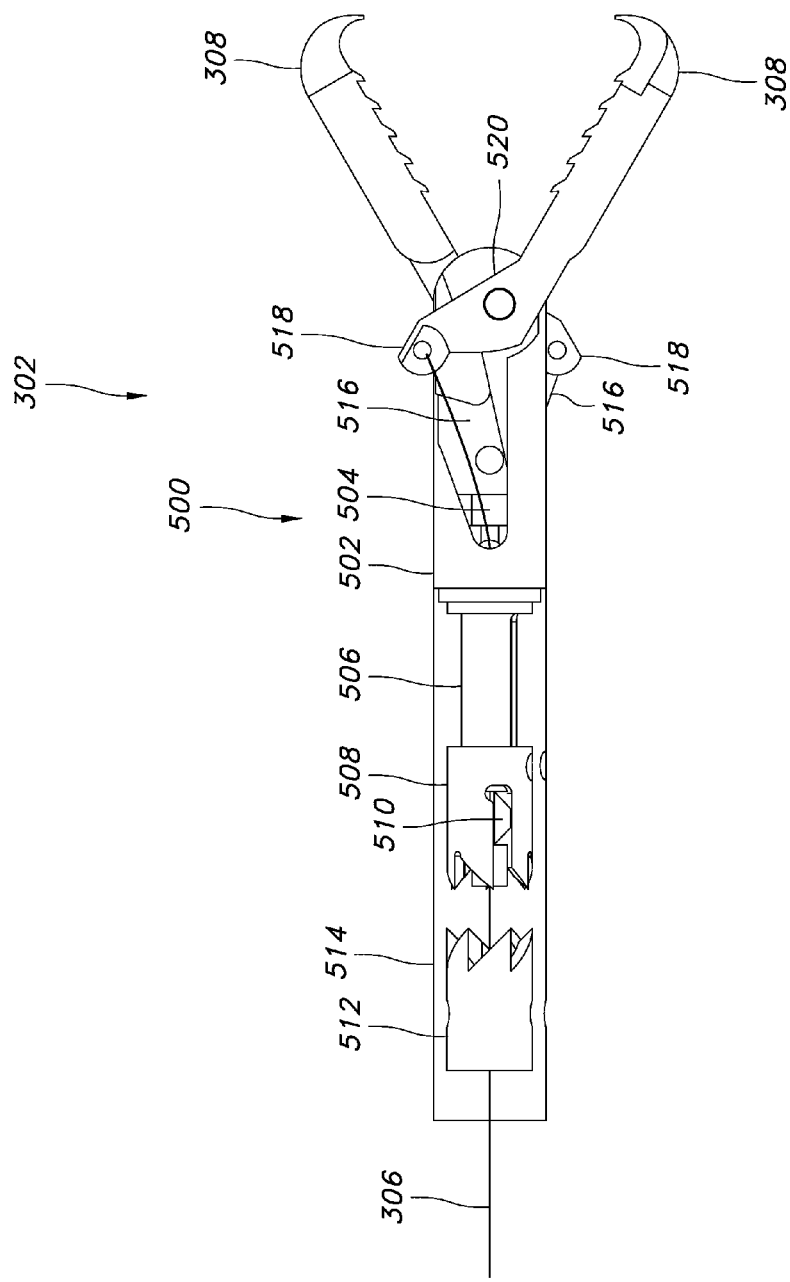
FIG. 5 illustrates one embodiment of a grasping head and a portion of a translating member of the grasping device of FIG. 3 shown in an open position.

FIG. 5 illustrates one embodiment of a grasping head 302 and a portion of a translating member 306 of the grasping device 300. The grasping head 302 may comprise an outer tube 514, a clevis 502, jaw members 308 and an actuating mechanism 500. The actuating mechanism 500 may include various other components to alternately open and close the jaw members 308 in response to a proximally directed force exerted on the translating member 306.

Figure 6:
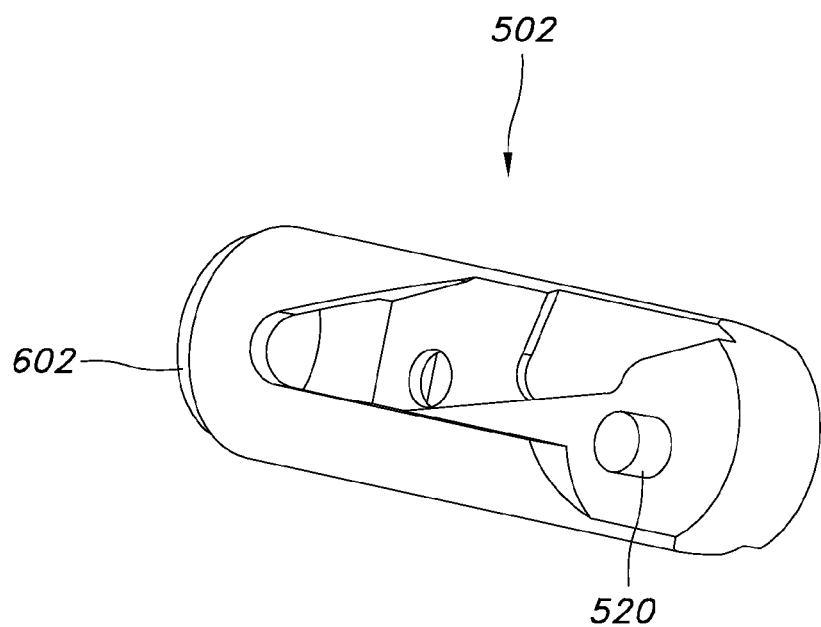
FIG. 6 illustrates one embodiment of a clevis component of the grasping head of FIG. 5.
Figure 7:
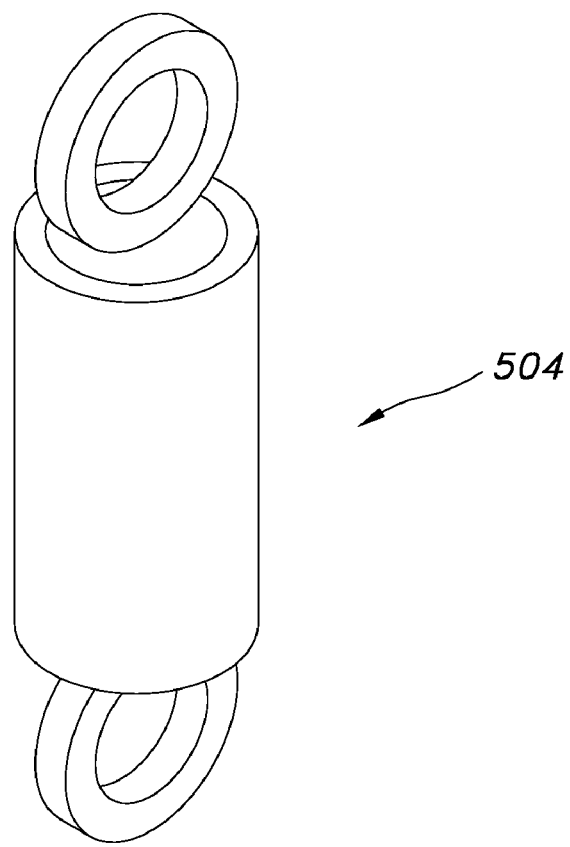
FIG. 7 illustrates one embodiment of a spring component of the grasping head of FIG. 5.
Figure 8:
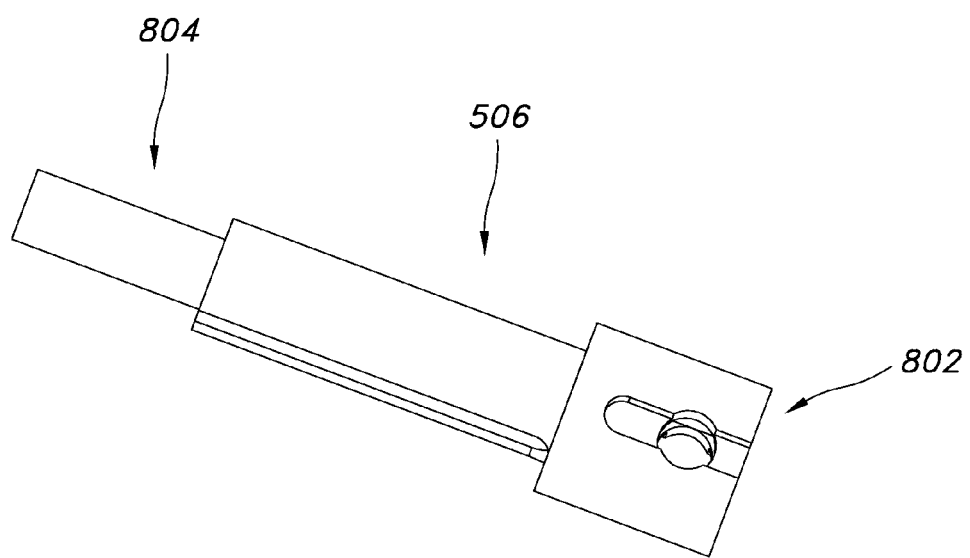
FIG. 8 illustrates one embodiment of a shuttle component of the grasping head of FIG. 5.

The jaw members 308 may be pivotably coupled to the clevis 502, for example, about a pin 520. FIG. 6 illustrates one embodiment of the clevis 502. Although only one instance of the pin 520 is shown, there may be a corresponding pin 520 in the opposite side of the clevis 502 for receiving the other jaw member 308. The clevis 502 may define a distal cavity 602 that may receive various other components. For example, a spring 504 may be positioned within the cavity 602 and may be coupled to the clevis 502 as well as a translatable shuttle 506. The spring 504 may bias the shuttle 506 distally. FIG. 7 illustrates one embodiment of the spring 504, while FIG. 8 illustrates one embodiment of the shuttle 506.

Figure 9:
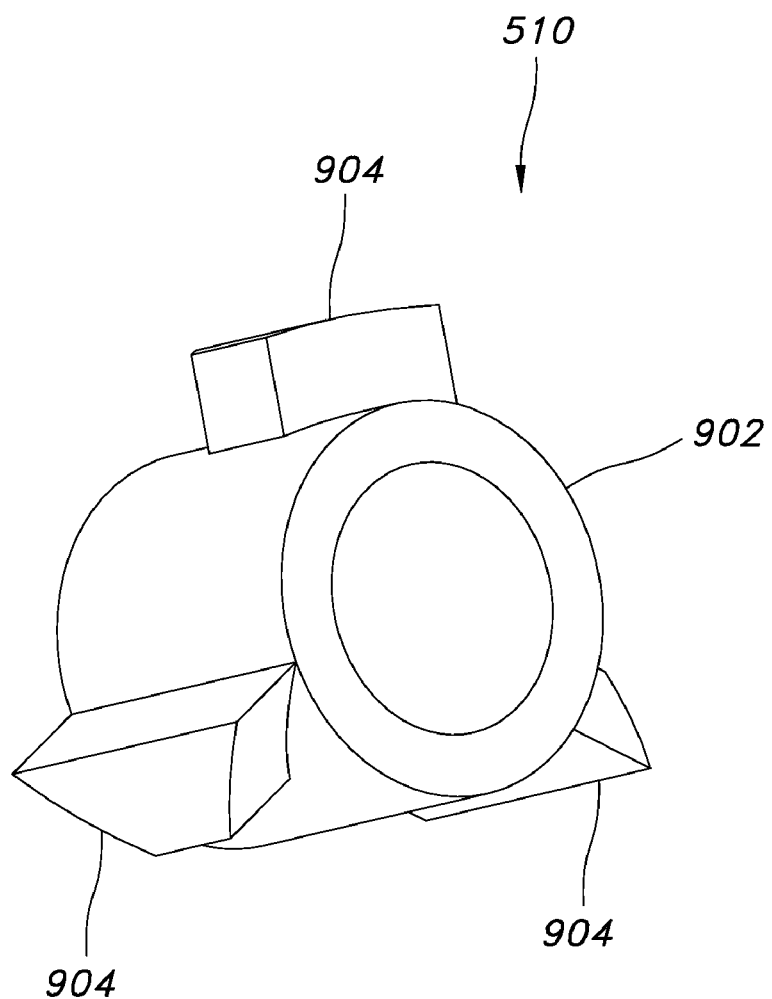
FIG. 9 illustrates one embodiment of a spinner disk component of the grasping head of FIG. 5.
Figure 10:
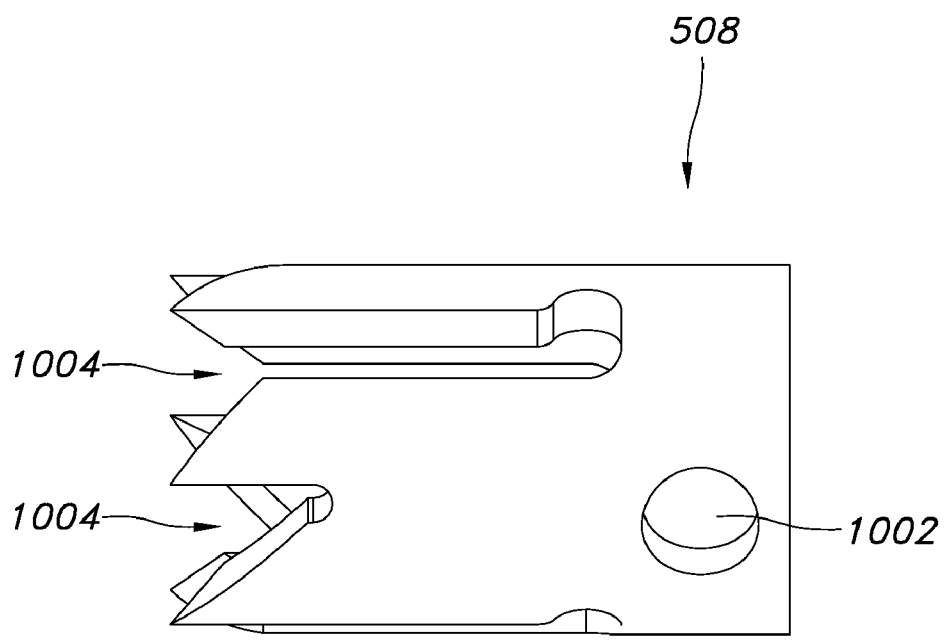
FIG. 10 illustrates one embodiment of an upper insert component of the grasping head of FIG. 5.
Figure 11:
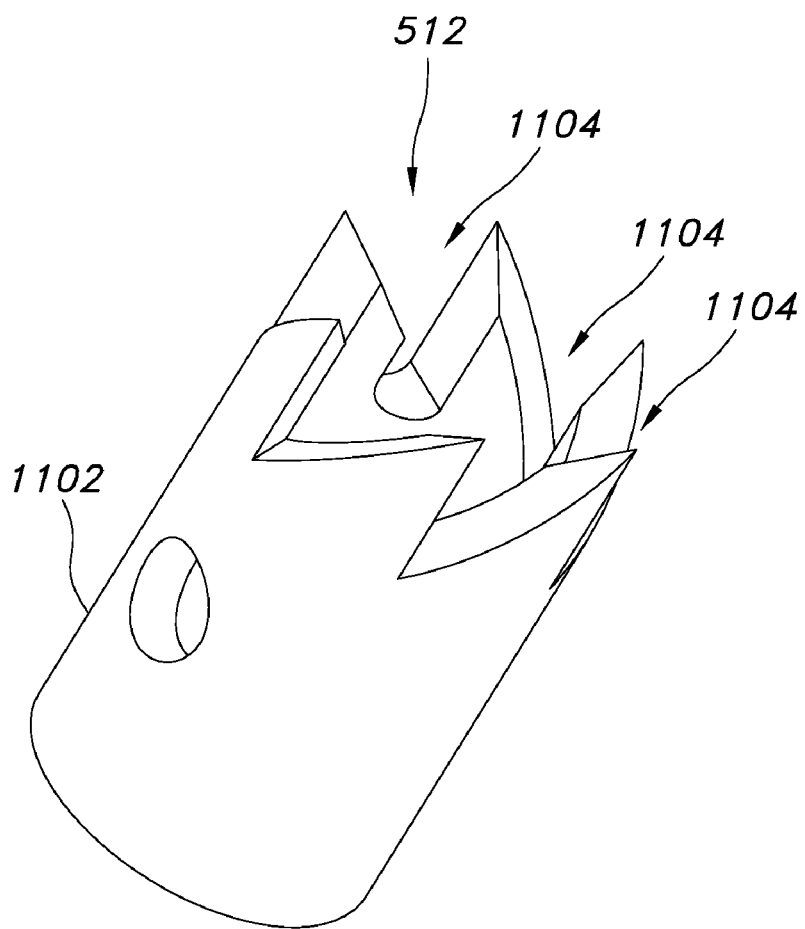
FIG. 11 illustrates one embodiment of a lower insert component of the grasping head of FIG. 5.

The shuttle 506 may also be coupled to the jaw members 308. For example, the jaw members 308 may comprise distally directed arms 518. Coupling members 516 may be positioned to couple the distally directed arms 518 of the jaw members 308 to a distal portion 802 of the shuttle 506. The coupling members 516 may be made from any suitable type of material and, according to various embodiments, may be wires or cables. Referring again to the shuttle 506, a proximal portion 804 of the shuttle may be coupled to a spinner disk 510. FIG. 9 illustrates one embodiment of the spinner disk 510. The spinner disk 510 may comprise a cylindrical body 902 with a plurality of radial spines 904 extending from the body 902. In use, the radial spines 904 of the spinner disk 510 may interact with an upper insert 508 and a lower insert 512. FIG. 10 illustrates one embodiment of the upper insert 508, while FIG. 11 illustrates one embodiment of the lower insert 512. The upper insert 508 may comprise alternating deep pockets 1004 and shallow pockets 1006. The lower insert 512 may comprise a plurality of pockets 1104, as shown.

Figure 12:
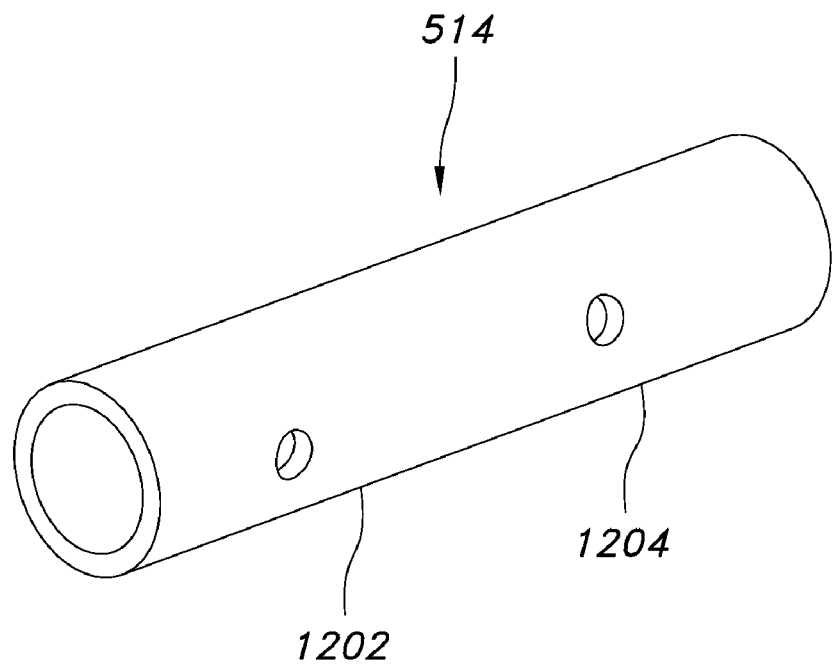
FIG. 12 illustrates one embodiment of the outer tube component of the grasping head of FIG. 5.

The upper and lower inserts, 508, 512 may be contained within and coupled to the outer tube 514. FIG. 12 illustrates one embodiment of the outer tube 514. The inserts 508, 512 may be coupled to the outer tube 514 according to any suitable manner. For example, upper insert 508 may define a hole 1002, while lower insert 512 may define a hole 1102. The outer tube 514 may define corresponding holes 1204, 1202. Pins (not shown) may be positioned through holes 1204 and 1002 and through holes 1202 and 1102 to hold the upper and lower inserts 508, 512 in place.

Figure 13:
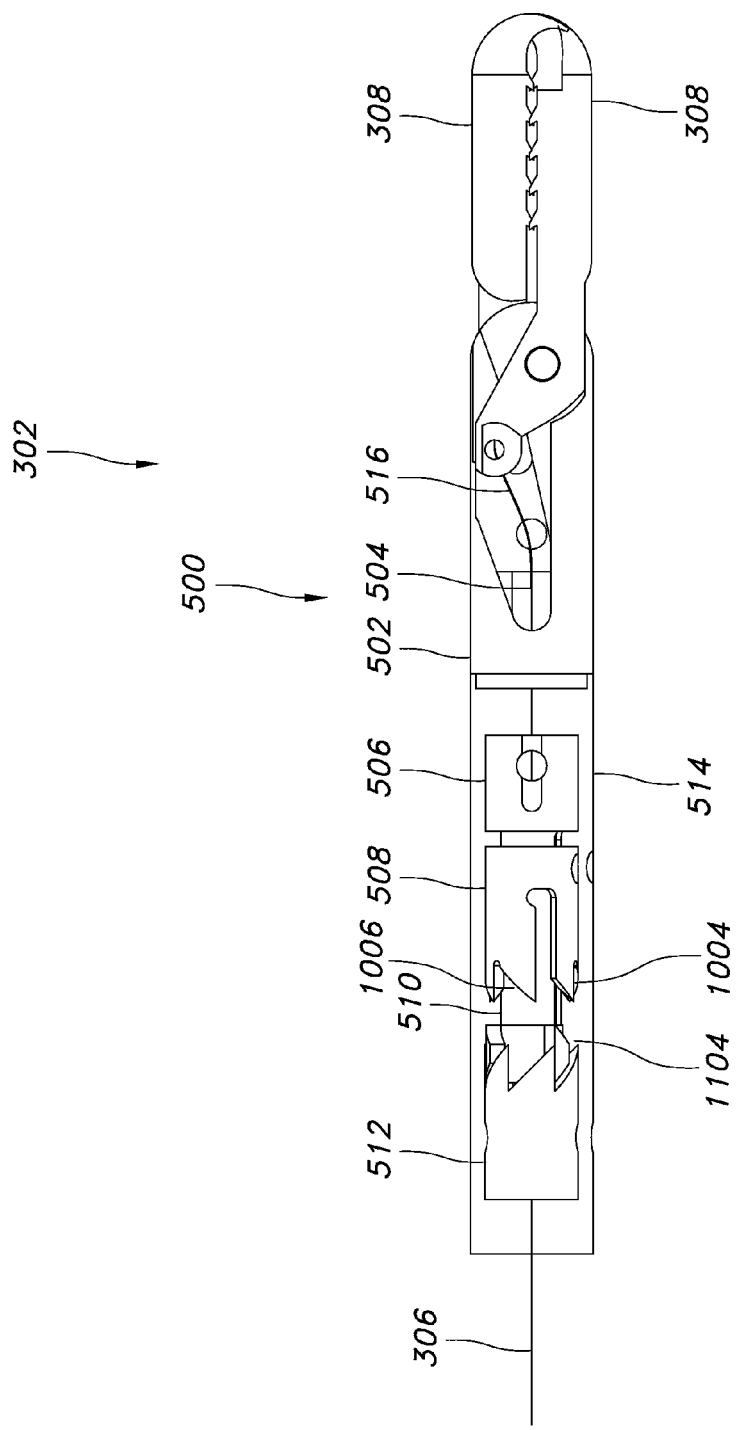
FIG. 13 illustrates one embodiment of the grasping head and translating member of the grasping device of FIG. 3 transitioning between the open position of FIG. 5 and a closed position.
Figure 14:
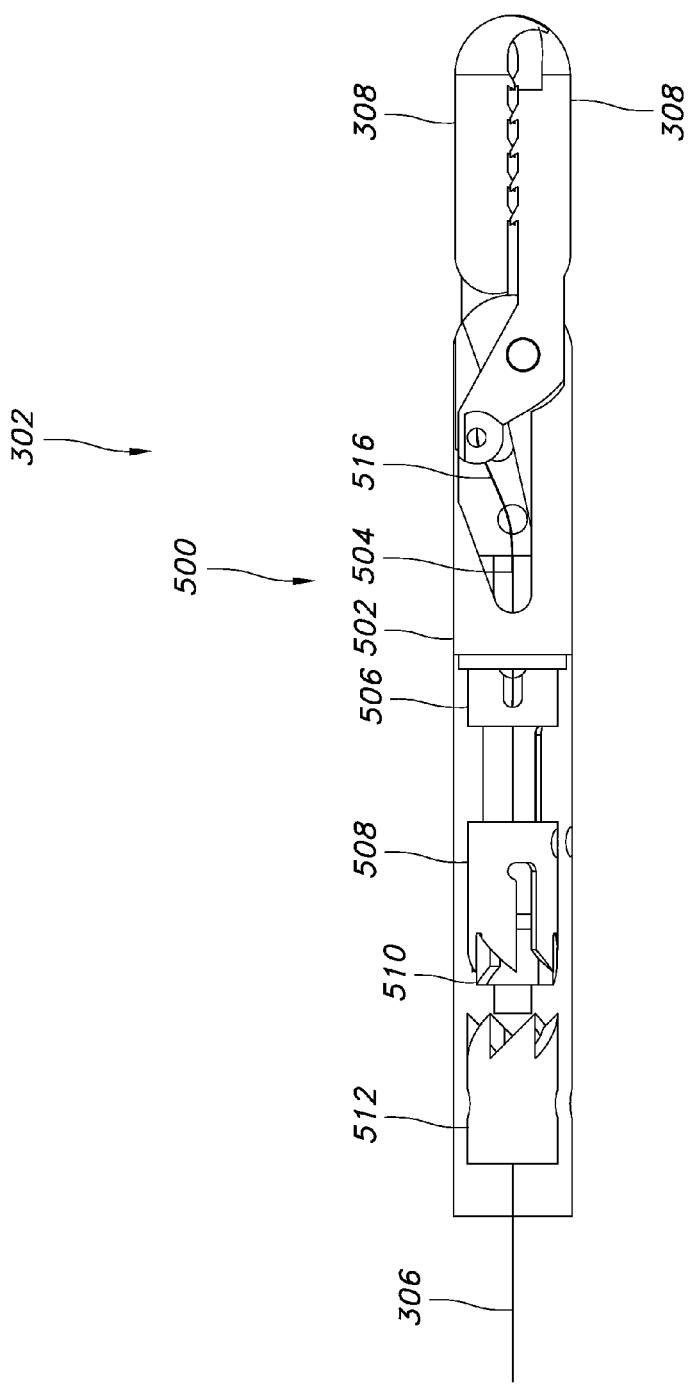
FIG. 14 illustrates one embodiment of the grasping head and translating member of the grasping device of FIG. 3 in a closed and locked position.

Referring back to FIG. 5, the grasping head 302 is shown with the jaw members 308 in the open position. The biasing force provided by the spring 504 pulls the shuttle 506, and the spinner disk 510 distally. As shown, the spines 904 of the spinner disk 510 are positioned within the deep pockets 1004 of the upper insert 508. To transition the jaw members 308 to the closed position, the clinician may exert a proximally directed force on the translating member 306. FIG. 13 illustrates one embodiment of the grasping head 302 and translating member 306 transitioning between the open position of FIG. 5 and a closed position. When the translating member 306 is pulled proximally, it may exert a proximal force on the shuttle 506, which may translate proximally. This may exert a proximal force on the coupling members 516, which may cause the jaw members 308 to close, as shown. Proximal motion of the shuttle 506 may also cause the spines 904 of the spinner disk 510 to exit the deep pockets 1004 of the upper insert 508. As the shuttle 506 is pulled further in the proximal direction, the spines 904 of the spinner disk 510 may contact the pockets 1104 of the lower insert 512. The pockets 1104 may be shaped to cause the spinner disk 510 to rotate. As a result, the spines 904 may no longer be aligned with the deep pockets 1004 of the upper insert, but may instead be aligned with the shallow pockets 1106. The clinician may then release the proximal force on the translating member 306. When this occurs, the biasing force of the spring 504 may pull the shuttle 506 and the spinner disk 510 distally. Because of the new alignment of the spinner disk 510, its spines 904 may be received by the shallow pockets 1006 of the upper insert 508, as shown in FIG. 14. This may hold the spinner disk 510 and the shuttle 506 in a more proximal position than the one shown in FIG. 5. As a result, the shuttle 506 may maintain its proximal force on the coupling members 516, which may, in turn, maintain the jaw members 308 in a closed and locked position.

The jaw members 308 may be re-opened when the clinician again exerts a proximally directed force on the translating member 306. This may cause the shuttle 506 and spinner disk 510 to again translate proximally. The pockets 1104 of the lower insert 512 may cause the spinner disk 510 to rotate, this time so that the spines 904 are re-aligned with the deep pockets 1004 of the upper insert 508. When the force on the translating mechanism 306 is released, the shuttle 506 and spinner disk 510 may translate distally to the position shown in FIG. 5, where the spines 904 are received by the deep pockets 1004. As the shuttle 506 translates to this proximal position, its proximally directed force on the coupling members 516 may relax, allowing the jaw members 308 to open.

Figure 15:
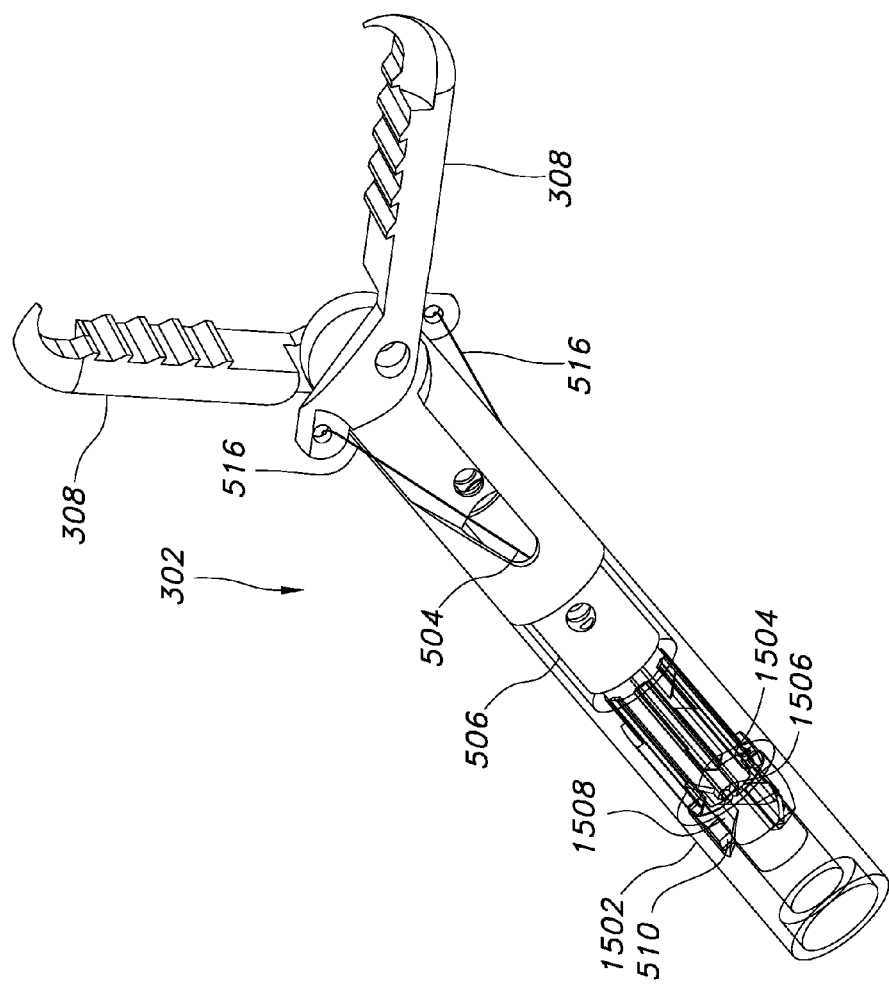
FIG. 15 illustrates an alternate embodiment of the grasping head of the grasping device of FIG. 3.

FIG. 15 illustrates an alternate embodiment of the grasping head 302 of the grasping device 300. As shown, the grasping head 302 may comprise an outer tube 1502. Instead of having upper and lower inserts 508 and 512, the outer tube 1502 may define deep pockets 1504 and shallow pockets 1506 corresponding to the deep pockets 1004 and shallow pockets 1006 described above. The outer tube 1502 may also comprise pockets 1508 corresponding to the pockets 1104 of the lower insert 512. The embodiment shown in FIG. 15 may operate in a manner similar to that described above with respect to FIGS. 3-14. Although several embodiments of the actuating mechanism 500 are illustrated above, it will be appreciated that other configurations may be used as well. For example, the spring 504 may be configured to bias the shuttle 506 proximally instead of distally. This may cause the positions of the upper and lower inserts 508 and 512 to be reversed.

In various embodiments, surgical instruments utilizing various embodiments of the grasping device 300 may be employed in conjunction with a flexible endoscope, such as a GIF-100 model available from Olympus Corporation, for example. In at least one such embodiment, the endoscope, a laparoscope, or a thoracoscope, for example, may be introduced into the patient trans-anally through the colon, the abdomen via an incision or keyhole and a trocar, or trans-orally through the esophagus, for example. These devices may assist the clinician to guide and position the grasping device 300 near the tissue treatment region to treat diseased tissue on organs such as the liver, for example. In another embodiment, these devices may be positioned to treat diseased tissue near the gastrointestinal (GI) tract, esophagus, and/or lung, for example. In various embodiments, the endoscope may comprise a flexible shaft where the distal end of the flexible shaft may comprise a light source, a viewing port, and at least one working channel. In at least one such embodiment, the viewing port may transmit an image within its field of view to an optical device such as a charge coupled device (CCD) camera within the endoscope, for example, so that an operator may view the image on a display monitor (not shown).

It will be appreciated that the terms "proximal" and "distal" are used herein with reference to a clinician manipulating an end of an instrument extending from the clinician to a surgical site (e.g., through a trocar, through a natural orifice, through an open surgical site, etc.). The term "proximal" refers to the portion closest to the clinician, and the term "distal" refers to the portion located away from the clinician. It will be further appreciated that for conciseness and clarity, spatial terms such as "vertical," "horizontal," "up," and "down" may be used herein with respect to the drawings. However, surgical instruments are used in many orientations and positions, and these terms are not intended to be limiting and absolute.

While several embodiments have been illustrated and described, and while several illustrative embodiments have been described in considerable detail, the embodiments are not intended to restrict or in any way limit the scope of the appended claims to such detail. Additional advantages and modifications may readily appear to those skilled in the art. Those of ordinary skill in the art will readily appreciate the different advantages provided by these various embodiments.

While several embodiments have been described, it should be apparent, however, that various modifications, alterations and adaptations to those embodiments may occur to persons skilled in the art with the attainment of some or all of the advantages of the embodiments. For example, according to various embodiments, a single component may be replaced by multiple components, and multiple components may be replaced by a single component, to perform a given function or functions. This application is therefore intended to cover all such modifications, alterations and adaptations without departing from the scope of the appended claims.

The devices disclosed herein may be designed to be disposed of after a single use, or they may be designed to be used multiple times. In either case, however, the device may be reconditioned for reuse after at least one use. Reconditioning may include a combination of the steps of disassembly of the device, followed by cleaning or replacement of particular pieces, and subsequent reassembly. In particular, the device may be disassembled, and any number of particular pieces or parts of the device may be selectively replaced or removed in any combination. Upon cleaning and/or replacement of particular parts, the device may be reassembled for subsequent use either at a reconditioning facility, or by a surgical team immediately prior to a surgical procedure. Those of ordinary skill in the art will appreciate that the reconditioning of a device may utilize a variety of different techniques for disassembly, cleaning/replacement, and reassembly. Use of such techniques, and the resulting reconditioned device, are all within the scope of the present application.

Preferably, the embodiments described herein will be processed before surgery. First a new or used instrument is obtained and, if necessary, cleaned. The instrument may then be sterilized. In one sterilization technique, the instrument is placed in a closed and sealed container, such as a plastic or TYVEK® bag. The container and instrument are then placed in a field of radiation that may penetrate the container, such as gamma radiation, x-rays, or higher energy electrons. The radiation kills bacteria on the instrument and in the container. The sterilized instrument may then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials do not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The embodiments are not to be construed as limited to the particular embodiments disclosed. The embodiments are therefore to be regarded as illustrative rather than restrictive. Variations and changes may be made by others without departing from the scope of the claims. Accordingly, it is expressly intended that all such equivalents, variations and changes that fall within the scope of the claims be embraced thereby.

In summary, numerous benefits have been described which result from employing the concepts described herein. The foregoing description of the one or more embodiments has been presented for purposes of illustration and description. It is not intended to be exhaustive or limiting to the precise form disclosed. Modifications or variations are possible in light of the above teachings. The one or more embodiments were chosen and described in order to illustrate principles and practical applications to thereby enable one of ordinary skill in the art to utilize the various embodiments and with various modifications as are suited to the particular use contemplated. It is intended that the claims submitted herewith define the overall scope.

What is claimed is:

1. A surgical grasping device, the device comprising:
a clevis;
a first jaw member pivotably coupled to the clevis;
a second jaw member pivotably coupled to the clevis;
an actuating mechanism coupled to the clevis, the first jaw member and the second jaw member, wherein the actuating mechanism comprises:
a shuttle, wherein the shuttle is coupled to the first jaw member by a first coupling member, wherein the shuttle is coupled to the second jaw member by a second coupling member, and wherein a proximal portion of the shuttle is coupled to the translating member;
a spring coupled to the shuttle and the clevis, wherein the spring is positioned to bias the shuttle distally;
a spinner disk coupled to the proximal portion of the shuttle, wherein the spinner disk comprises a plurality of radial spines;
a hollow upper insert to receive the spinner disk, wherein the upper insert defines a first plurality of pockets shaped to receive the plurality of radial spines to hold the spinner disk in a distal position and a second plurality of pockets shaped to receive the plurality of radial spines to hold the spinner disk in a proximal position; and
a translating member coupled to and extending proximally from the actuating mechanism, wherein the actuating mechanism is configured to cause the first jaw member and the second jaw member to close in response to a first proximally directed force received via the translating member, and wherein the actuating mechanism is also configured to cause the first jaw member and the second jaw member to open in response to a subsequent proximally directed force received via the translating member.

2. The surgical grasping device of claim 1, further comprising a removable hollow shaft extending proximally from the translating member.

3. The surgical grasping device of claim 2, wherein the hollow shaft is flexible.

4. The surgical grasping device of claim 1, further comprising an outer tube enclosing at least a portion of the actuating mechanism.

5. The surgical device of claim 1, wherein the translating member comprises a cable.

6. The surgical device of claim 1, wherein the translating member comprises a rigid member.

7. The surgical device of claim 1, wherein the actuating mechanism further comprises a hollow lower insert positioned proximally relative to the upper insert and configured to receive the spinner disk, wherein the hollow lower insert defines a third plurality of pockets shaped to receive the plurality of radial spines and rotate the spinner disk from a first position where the radial spines are aligned with the first plurality of pockets of the upper insert to a second position where the radial spines are aligned with the second plurality of pockets of the upper insert.

8. The surgical device of claim 1, wherein the first coupling member comprises a cable.

9. The surgical device of claim 1, wherein the first coupling member is rigid.

10. A surgical grasping device, the device comprising:
a clevis;
a first jaw member pivotably coupled to the clevis;
a second jaw member pivotably coupled to the clevis;
an actuating mechanism coupled to the clevis, the first jaw member and the second jaw member, wherein the actuating mechanism comprises:
  a shuttle, wherein the shuttle is coupled to the first jaw member by a first coupling member, wherein the shuttle is coupled to a second jaw member by a second coupling member, and wherein a proximal portion of the shuttle is coupled to the translating member;
  a spring coupled to the shuttle and the clevis, wherein the spring is positioned to bias the shuttle distally;
  a spinner disk coupled to a proximal portion of the shuttle, wherein the spinner disk comprises a plurality of radial spines;
  an outer tube enclosing at least a portion of the shuttle, the spring and the spinner disk, wherein the outer tube defines a first plurality of pockets shaped to receive the plurality of radial spines to hold the spinner disk in a distal position and a second plurality of pockets shaped to receive the plurality of radial spines to hold the spinner disk in a proximal position; and
a translating member coupled to and extending proximally from the actuating mechanism, wherein the actuating mechanism is configured to cause the first jaw member and the second jaw member to close in response to a first proximally directed force received via the translating member, and wherein the actuating mechanism is also configured to cause the first jaw member and the second jaw member to open in response to a subsequent proximally directed force received via the translating member.

11. The surgical device of claim 10, wherein the outer tube further defines a third plurality of pockets positioned proximally relative to the first and second plurality of pockets, wherein the third plurality of pockets are shaped to receive the plurality of radial spines and rotate the spinner disk from a first position where the radial spines are aligned with the first plurality of pockets to a second position where the radial spines are aligned with the second plurality of pockets.

12. The surgical device of claim 10, wherein the translating member comprises a cable.

13. The surgical device of claim 10, wherein the translating member comprises a rigid member.

14. The surgical grasping device of claim 10, further comprising a removable hollow shaft extending proximally from the translating member.

15. The surgical grasping device of claim 14, wherein the hollow shaft is flexible.

* * * * *